(12) United States Patent
Jardieu et al.

(10) Patent No.: US 6,703,018 B2
(45) Date of Patent: Mar. 9, 2004

(54) METHOD OF TREATMENT USING HUMANIZED ANTI-CD11A ANTIBODIES

(75) Inventors: Paula M. Jardieu, San Francisco, CA (US); Leonard G. Presta, San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 17 days.

(21) Appl. No.: 09/795,798

(22) Filed: Feb. 28, 2001

(65) Prior Publication Data

US 2003/0207336 A1 Nov. 6, 2003

Related U.S. Application Data

(62) Division of application No. 09/420,745, filed on Oct. 20, 1999, now abandoned, which is a continuation of application No. 08/974,899, filed on Nov. 20, 1997, now Pat. No. 6,037,454.
(60) Provisional application No. 60/031,971, filed on Nov. 27, 1996.

(51) Int. Cl.$^7$ ................ A61K 39/395; A61K 39/385; C12P 21/08; C07K 16/34
(52) U.S. Cl. ................ 424/133.1; 424/141.1; 424/143.1; 424/144.1; 424/152.1; 424/153.1; 424/193.1; 530/387.3; 530/388.75; 530/391.7
(58) Field of Search .............. 424/130.1, 133.1, 424/141.1, 143.1, 152.1, 153.1, 159.1, 154.1, 172.1, 173.1, 193.1, 144.1; 530/367.1, 388.7, 388.73, 388.75, 387.3, 391.1, 391.3, 391.7

(56) References Cited

U.S. PATENT DOCUMENTS

| | | | |
|---|---|---|---|
| 4,816,567 A | | 3/1989 | Cabilly et al. |
| 5,622,700 A | * | 4/1997 | Jardieu et al. |
| 6,037,454 A | * | 3/2000 | Jardieu et al. |

FOREIGN PATENT DOCUMENTS

| EP | 364690 | 4/1990 |
|---|---|---|
| EP | 440351 | 8/1991 |
| EP | 699755 | 3/1996 |
| WO | WO 91/09967 | 7/1991 |
| WO | WO 91/16927 | 11/1991 |
| WO | WO 93/01296 | 1/1993 |
| WO | WO 94/04188 | 3/1994 |
| WO | WO 95/23813 | 9/1995 |
| WO | WO 96/32478 | 10/1996 |
| WO | WO 96/36359 | 11/1996 |
| WO | WO 97/31024 | 8/1997 |

OTHER PUBLICATIONS

Dedrick et al. Anti–adhesion efalizumab, a humanized anti–CD11a monoclonal antibody. Transpl Immunol. 9(2–4):181–6, 2000.*
Van Noort JM, Amor S. Cell biology of autoimmune diseases. Int Rev Cytol. 178:127–206, 1998.*
Ward PA, Mulligan MS. Blocking of adhesion molecules in vivo as anti–inflammatory therapy. Ther Immumol 1(3):165–171, 1994.*
Chothia, C. et al., "Conformations of immunoglobulin hypervariable regions" *Nature* 342 (6252):877–883. (1989).
Dantal et al., "Use of Monoclonal Antibodies in Human Transplantation" *Current Opinion in Immunology* 3:740–747 (1991).
Edwards et al., "Identification of Amino Acids in the CD11a I–domain Important for Binding of the Leukocyte Function–associated Antigen–1 (LFA–1) to Intercellular Adhesion Molecule–1 (ICAM–1)" *Journal of Biological Chemistry* 270 (21):12635–12640 May 26, 1995).
Fischer et al., "Reduction of Graft Failure by a Monoclonal Antibody (Anti–LFA–1 CD11a) After HLA Nonidentical Bone Marrow Transplantation in Children with Immunodeficiencies, Osteopetrosis, and Fanconi's Anemia" *Blood* 77 (2) :249–256 (Jan. 15, 1991).
He et al., "Effect of LFA–1 and ICAM–1 antibody treatment on murine corneal allograft survival" *Invest. Ophthalmol. Vis. Sci.* 35:3218–3225 (1994).
Riechmann et al., "Reshaping Human Antibodies for Therapy" *Nature* 332:323–327 (Mar. 24, 1988).
Werther et al., "Humanization of an Anti–Lymphocyte Function–Associated Antigen (LFA)–1 Monoclonal Antibody and Reengineering of the Humanized Antibody for Binding to Rhesus LFA–1" *J. of Immunology* 157:4986–4995 (1996).
Wognum et al., "Immunochemical Analysis of Monoclonal Antibodies to Human Erythropoietin" *Exp. Hematology* 18:228–233 (1990).
Barry, J., "Immunosuppressive drugs in renal transplantation. A review of the regimens" *Drugs* 44:554–556 (1992).
Brown, Jr. et al., "Anti–Tac–H, a humanized antibody to the interleukin 2 receptor, prolongs primate cardiac allograft survival" *Proc. Natl. Acad. Sci. USA* 88:2663–2667 (1991).
Carter et al., "Engineering Subtilisin BPN' for Site–Specific Proteolysis" *Proteins: Struct. Funct., Genet.* 6:240–248 (1989).
Carter et al., "Humanization of an anti–p185$^{HER2}$ antibody for human cancer therapy" *Proc. Natl. Acad. Sci.* 89:4285–4289 (1992).
Cavazzana–Calvo et al., "Prevention of bone marrow and cardiac graft rejection in an H–2 haplotype disparate mouse combination by an anti–LFA–1 antibody" *Transplantation* 59:1576–1582 (1995).

(List continued on next page.)

Primary Examiner—Christina Chan
Assistant Examiner—Maher Haddad
(74) Attorney, Agent, or Firm—Lee Tan

(57) ABSTRACT

Humanized anti-CD11a antibodies and various uses therefor are disclosed. The humanized anti-CD11a antibody may bind specifically to human CD11a I-domain, have an IC50 (nM) value of no more than about 1 nM for preventing adhesion of Jurkat cells to normal human epidermal keratinocytes expressing ICAM-1, and/or an IC50 (nM) value of no more than about 1 nM in the mixed lymphocyte response assay.

11 Claims, 4 Drawing Sheets

OTHER PUBLICATIONS

Champe et al., "Monoclonal antibodies that block the activity of leukocyte function–associated antigen 1 recognize three discrete epitopes in the inserted domain of CD11a" *Journal of Biological Chemistry* 270:1388–1384 (1995).

Cunningham et al., "High–Resolution Epitope Mapping of hgH–Receptor Interactions by Alanine–Scanning Mutagenesis" *Science* 244:1081–1085 (Jun. 1989).

Cunningham et al., "Receptor and Antibody Epitopes in Human Growth Hormone Identified by Homolog–Scanning Mutagenesis" *Science* 243:1330–1336 (1989).

Dougherty et al., "The role of monocyte lymphocyte function–associated antigen 1 (LFG–1) in accessory cell function" *European Journal of Immunology* 17:943–947 (1987).

Dustin et al., "Induction By IL and Interferon–γ: Tissue Distribution, Biochemistry, and Function of a Natural Adherence Molecule (ICAM–1)" *The Journal of Immunology* 137(1):245–254 (Jul. 1, 1986).

Eaton et al., "Construction and characterization of an active factor VIII variant lacking the central one–third of the molecule" *Biochemistry* 25:8343–8347 (1986).

Eigenbrot et al., "X–Ray Structure of Fragments From Binding and Nonbinding Versions of a Humanized Anti–CD18 Antibody: Structural Indications of the Key Role of $V_H$ Residues 59 to 65" *Proteins: Structure, Function, and Genetics* 18:49–62 (1994).

Eigenbrot et al., "X–ray structure of the antigen–binding domains from three variants of humanized anti–p185$^{HER2}$ antibody 4D5 and comparison with molecular modeling" *J. Mol. Biol.* 229:969–995 (1993).

Ellison et al., "The nucleotide sequence of a human immunoglobulin $C_{γ1}$ gene" *Nucleic Acids Research* 10 (13):4071–4079 (1982).

Fischer et al., "Role of the LFA–1 Molecule in Cellular Interactions Required For Antibody Production in Humans" *The Journal of Immunology* 136(9):3198–3203 (May 1, 1986).

Gorman et al., "High efficiency DNA–mediated transformation of primate cells" *Science* 221:551–553 (1983).

Gorman et al., "Transient Production of Proteins Using and Adenovirus Transformed Cell Line" *DNA Prot. Eng. Tech.* 2(1):3–10 (1990).

Graham et al., "Characteristics of a Human Cell Line Transformed by DNA from Human Adenovirus Type 5" *J. Gen. Virol.* 36:59–74 (1977).

Hawkins et al., "Selection of Phage Antibodies by Binding Affinity Mimicking Affinity Maturation" *J. Mol. Biol.* 226:889–896 (1992).

Hildreth et al., "A Human Lymphocyte–associated Antigen Involved in Cell–mediated Lympholysis" *European Journal of Immunology* 13:202–208 (1983).

Hildreth et al., "The human lymphocyte function–associated (HLFA) antigen and a related macrophage differentiation antigen (HMac–1) : functional effects of subunit–specific monoclonal antibodies" *J. Immunol.* 134:3272–3280 (1985).

Hourmant et al., "Administration of an Anti–CD11a Monoclonal Antibody in Recipients of Kidney Transplantation" *Transplantation* 58(3):377–380 (Aug. 1994).

Jones et al., "Replacing the Complementarity–determining Regions in a Human Antibody with Those From a Mouse" *Nature* 321:522–525 May 29, 1986).

Kabat et al. *Sequences of Proteins of Immunological Interest*, U.S. Dept. of Health and Human Services, NIH, 5th edition vol. 1:103–108, 324–331 (1991).

Kelley et al., "Characterization of Humanized Anti–p185$^{HER2}$ Antibody Fab Fragments Produced in *Escherichia coli*" *Protein Folding In Vivo and In Vitro*, Jeffrey L. Cleland, Washington, D.C.:American Chemical Society pps. 218–239 (1993).

Krensky et al., "The Functional Significance, Distibution, and Structure of LFA–1, LFA–2, and LFA–3: Cell Surface Antigens Associated with CTL–Target Interactions" *The Journal of Immunology* 131(2):611–616. (Aug. 1983).

Kunkel, T., "Rapid and Efficient Site–Specific Mutagenesis Without PhenotypicSelection" *Proc. Natl. Acad. Sci.* 82:488–492 (1985).

Kuypers et al., "Leukocyte Membrane Adhesion Proteins LFA–1, CR3 and p150,95: A Review of Functional and Regulatory Aspects" *Res. Immumol.* 140:461–486 (1989).

Larson et al., "Structure and Function of Leukocyte Integrins" *Immunological Reviews* 114:181–217 (1990).

Lo et al., "Two Leukocyte Receptors (CD11a/CD18 and CD11b/CD18) Mediate Transient Adhesion to Endothelium by Binding to Different Ligands" *The Journal of Immunology* 143(10):3325–3329 (Nov. 15, 1989).

Lowman et al., "Selecting High–Affinity Binding Proteins by Monovalent Phage Display" *Biochemistry* 30(45):10832–10838 (1991).

McCabe et al., "sICAM–1 Enhance Cytokine Production Stimulated by Alloantigen" *Cellular Immunology* 150:364–375 (1993).

McClure, H., "Nonhuman Primate Models for Human Disease" *Advances in Veterinary Science and Comparative Medicine* 28:267–304 (1984).

Nakakura et al., "Potent and Effective Prolongation by Anti–LFA–1 Monoclonal Antibody Monotherapy of Non–Primarily Vascularized Heart Allograft Survival in Mice Without T Cell Depletion" *Transplantation* 55(2):412–417 (Feb. 1993).

Nishihara et al., "Potent immunosuppressive effect of anti–LFA–1 monoclonal antibody on islet allograft rejection" *Transplantation Proc.* 27:372 (1995).

Parlevliet et al., "Monoclonal antibodies in rental transplation: a review" *Transplant Intl.* 5:234–246 (1992).

Presta et al., "Humanization of an Antibody Directed Against IgE" *J. Immunol.* 151(5):2623–2632 (Sep. 1, 1993).

Reimann et al., "Use of human leukocyte–specific monoclonal antibodies for clinically immunophenotyping lymphocytes of rhesus monkeys" *Cytometry* 17:102–108 (1994).

Saban et al., "Humanized Anti–IgE Monoclonal Antibody Mae25 Blocks Passive Sensitization of Rhesus Monkey Bladder In Vitro" *FASEB J.* (Abstract 3953) 8(5):A682 (Mar. 18, 1994).

Simmons et al., "ICAM, an adhesion ligand of LFA–1, is homologous to the neural cell adhesion molecule NCAM" *Nature* 331:624–627 (1988).

Staunton, D.E., et al., "Primary Structure of ICAM–1 Demonstrates Interaction between Members of the Immunoglobulin and Integrin Supergene Families" *Cell* 52:925–933 (1988).

Stoppa et al., "Anti–LFA1 Monoclonal Antibody (25.3) for Treatment of Steroid–resistant Grade III–IV Acute Graft–versus–host Disease" *Transplant International* 4:3–7 (1991).

Talento et al., "A single administration of LFA–1 antibody confers prolonged allograft survival" *Transplantation* 55:418–422 (1993).

Tanaka et al., "Prolonged inhibition of an antigen–specific IgE response in vivo by monoclonal antibody against lymphocyte function–associated antigen–1" *European Journal of Immunology* 25:1555–1558 (1995).

Tramontano et al., "Framework residue 71 is a major determinant of the position and conformation of the second hypervariable region in the $V_H$ domains of immunoglobulins" *J. Mol. Biol.* 215(1):175–182 (Sep. 5, 1990).

Van Dijken et al., "Evidence That Anti–LFA–1 in vivo Improves Engraftment and Survival After Allogeneic Bone Marrow Transplantation" *Transplantation* 49(5):882–886 (May 1990).

Verhoeyen et al., "Reshaping Human Antibodies: Grafting an Antilysozyme Activity" *Science* 239:1534–1536 (Mar. 25, 1988).

de Fougerolles et al., "Characterization of ICAM–2 and evidence for a third counter–receptor for LFA–1" *Journal of Experimental Medicine* 174:253–267 (1991).

de Fougerolles et al., "Characterization of the function of intercellular adhesion molecule (ICAM)–3 and comparison with ICAM–1 and ICAM–2 in immune responses" *Journal of Experimental Medicine* 179:619–629 (1994).

\* cited by examiner

```
              1         10        20        30        40
MHM24    DVQITQSPSYLAASPGETISINC[RASKTISKYLA]WYQEKPGKTNKLLIY
          ..        . . ....   .              .         ..
F(ab)-8  DIQMTQSPSSLSASVGDRVTITC[RASKTISKYLA]WYQQKPGKAPKLLIY
                                   ... .
humkI    DIQMTQSPSSLSASVGDRVTITC[RASQSISNYLA]WYQQKPGKAPKLLIY 60        70        80        90
MHM24    [SGSTLQS]GIPSRFSGSGSGTDFTLTISSLEPEDFAMYYC[QQHNEYPLT]
                   .              .    .     .            ...  .
F(ab)-8  [SGSTLQS]GVPSRFSGSGSGTDFTLTISSLQPEDFATYYC[QQHNEYPLT]
          .. .                                              . .. .
humkI    [AASSLES]GVPSRFSGSGSGTDFTLTISSLQPEDFATYYC[QQYNSLPWT]

100
MHM24    FGTGTKLELKR
             .  . .
F(ab)-8  FGQGTKVEIKR humkI    FGQGTKVEIKR        FIG._1A 1         10        20        30        40
MHM24    EVQLQQPGAELMRPGASVKLSCKASGYSFT[GHWMN]WVRQRPGQGLEWIG
           . ...  ..  ..   . ..     .              .   . .
F(ab)-8  EVQLVESGGGLVQPGGSLRLSCAASGYSFT[GHWMN]WVRQAPGKGLEWVG
                                    .. . ...                    .
humIII   EVQLVESGGGLVQPGGSLRLSCAASGFTFS[SYAMS]WVRQAPGKGLEWVS RhIgG1   EVQLVESGGGLVQPGGSLRLSCAASGYSFT[GHWMN]WVRQAPGKGLEWVG 50   a     60        70        80  abc      90
MHM24    [MIHPSDSETRLNQKFKD]KATLTVDKSSSSAYMQLSSPTSEDSAVYYCAR
                .             .. ..    .... . ..  ...      .
F(ab)-8  [MIHPSDSETRYNQKFKD]RFTISVDKSKNTLYLQMNSLRAEDTAVYYCAR
              . ...... . ....  .           . .
humIII   [VISGDGGSTYYADSVKG]RFTISRDNSKNTLYLQMNSLRAEDTAVYYCAR RhIgG1   [MIAPASSSTRYNQKFKD]RFTISVDKSKNTLYLQMNSLRAEDTAVYYCAR 100       110
MHM24    [GIYFYGTTYFDY]WGQGTTLTVSS
                         .
F(ab)-8  [GIYFYGTTYFDY]WGQGTLVTVSS
          .........
humIII   [G--------FDY]WGQGTLVTVSS RhIgG1   [GIYFYGTTYFDY]WGQGTLVTVSS        FIG._1B
```

```
                130         140         150         160         170
                 •           •           •           •           •
humCD11a    KGNVDLVFLFDGSMSLQPDEFQKILDFMKDVMKKLSNTSYQFAAVQF
rhCD11a       I
              β1                      α1                    β2
                180         190         200         210
                 •           •           •           •
humCD11a    STSYKTEFDFSDYVKRKDPDALLKHVKHMLLLTNTFGAINYVATEV
rhCD11a            Q           E
            β2'   α2         α3                   α4
                      230         240         250         260
                       •           •           •           •
humCD11a    FREELGARPDATKVLIIITDGEATDSGNIDAAKDIIRYIIGIGKHFQ
rhCD11a
                       β3                  α5         β4
                270         280         290         300         310
                 •           •           •           •           •
humCD11a    TKESQETLHKFASKPASEFVKILDTFEKLKDLFTELQKKIYVIE
rhCD11a                                                       A
                α6                  β5          α7
```
FIG._2
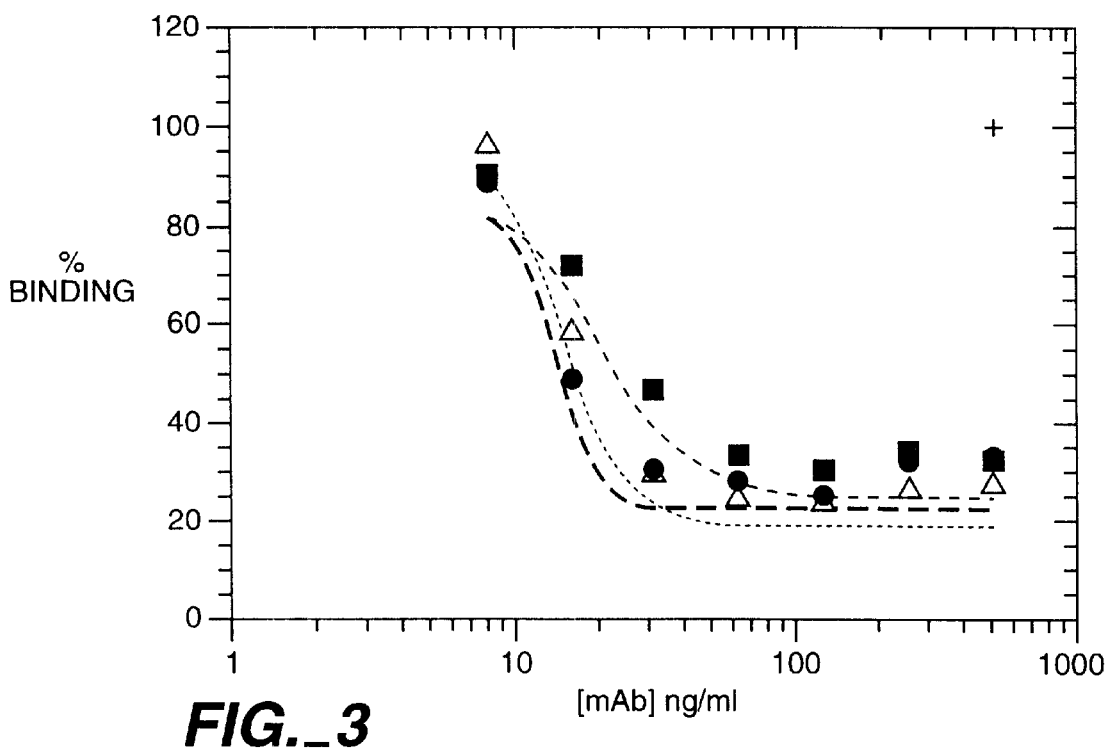
FIG._3

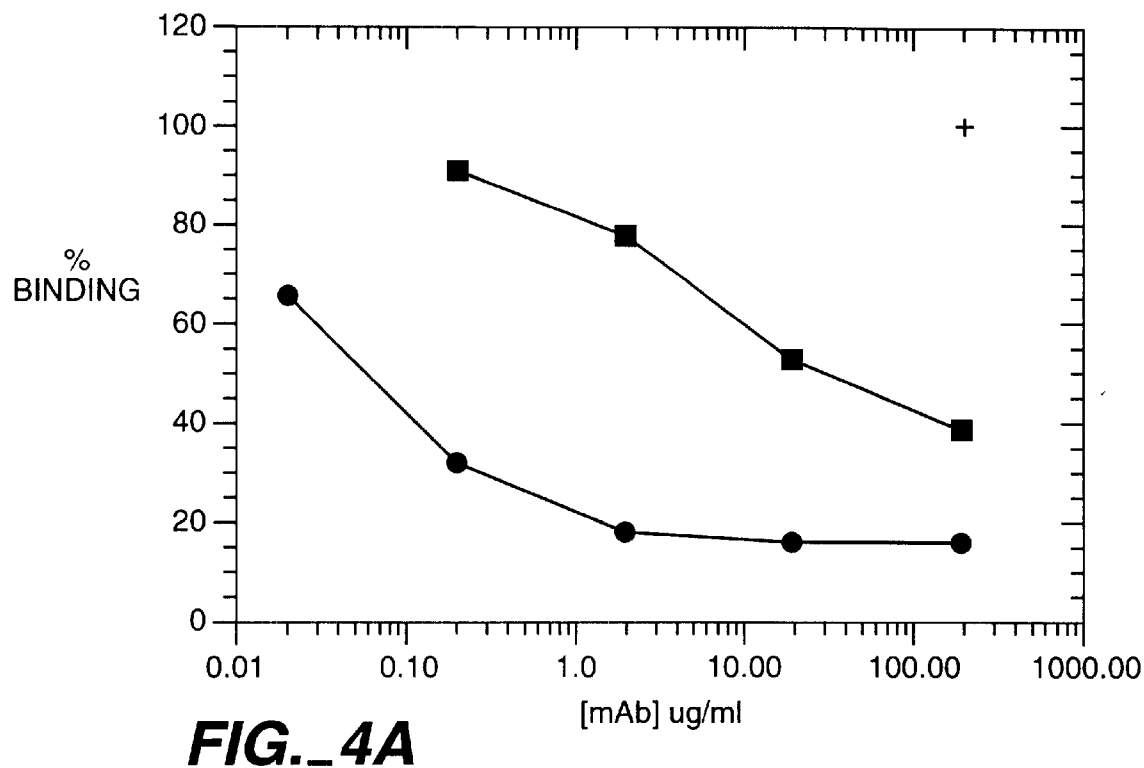
FIG._4A
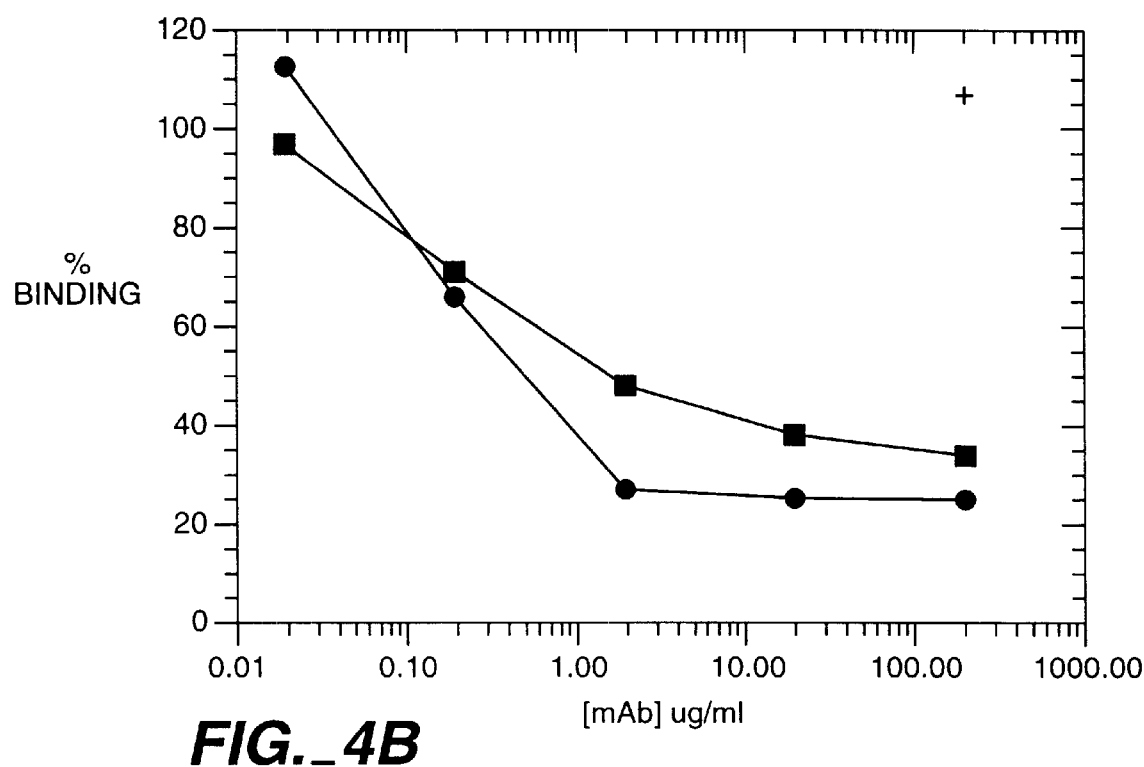
FIG._4B

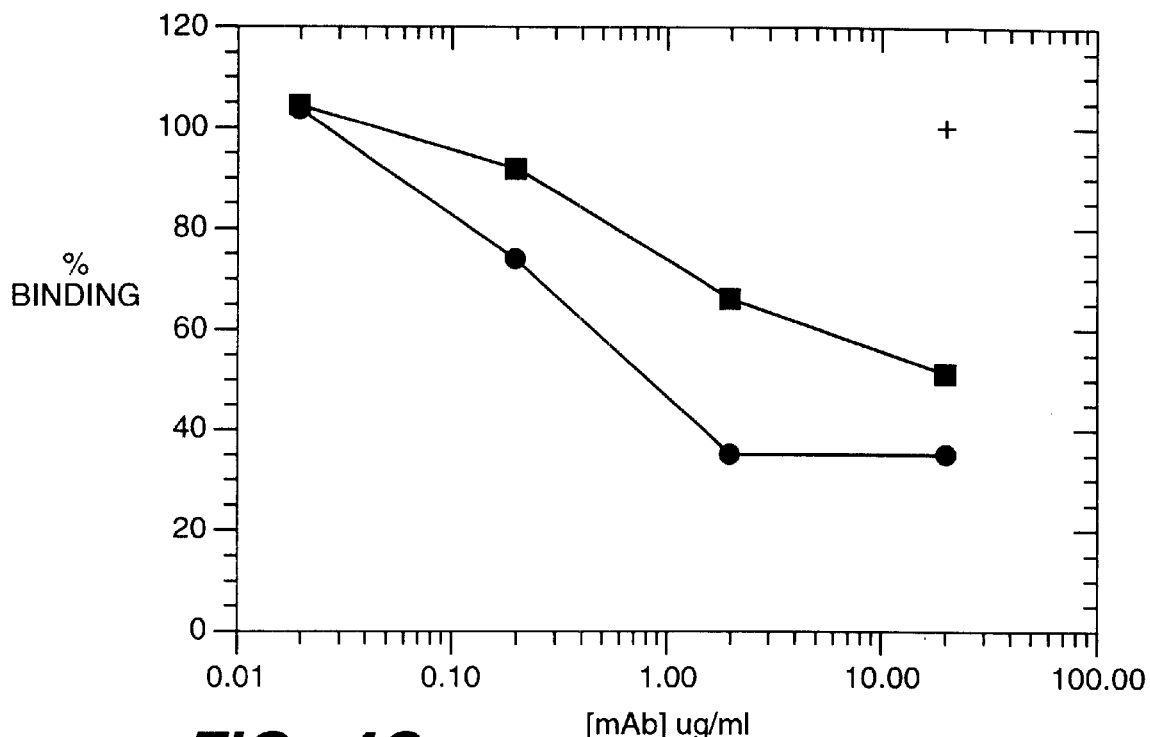
FIG._4C
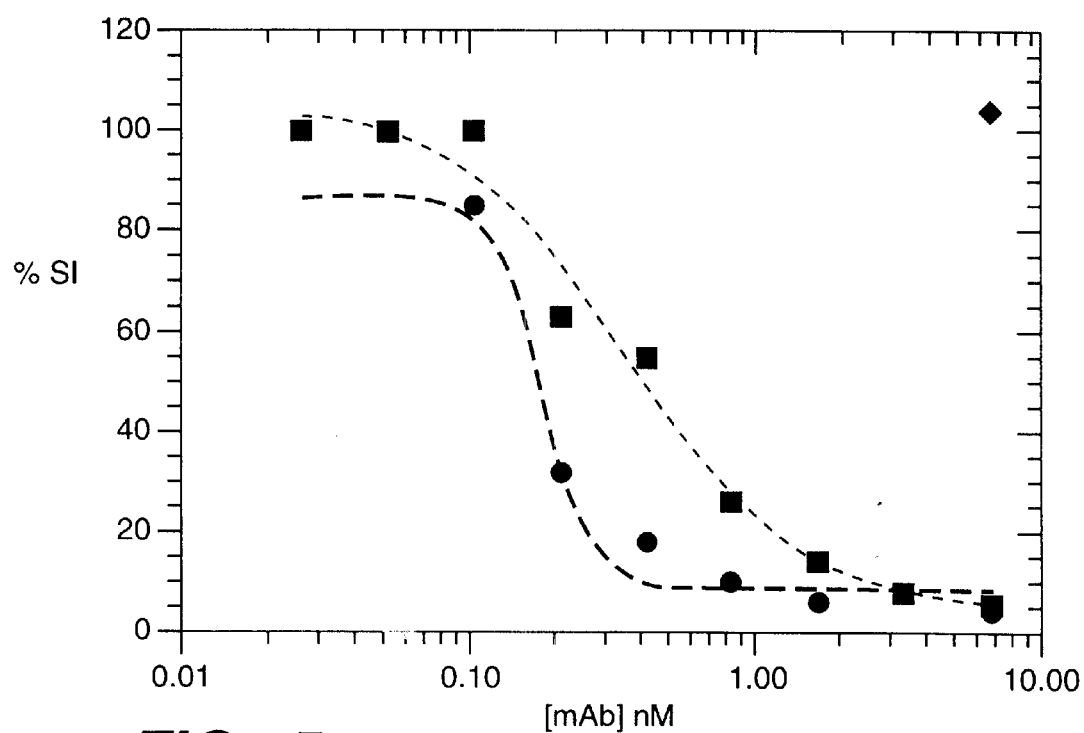
FIG._5

SEQUENCE LISTING (1) GENERAL INFORMATION:

(iii) NUMBER OF SEQUENCES: 71

(2) INFORMATION FOR SEQ ID NO: 1:

(i) SEQUENCE CHARACTERISTICS:
      (A) LENGTH: 108 amino acids (B) TYPE: Amino Acid
        (D) TOPOLOGY: Linear (xi) SEQUENCE DESCRIPTION: SEQ ID NO: 1:

Asp Val Gln Ile Thr Gln Ser Pro Ser Tyr Leu Ala Ala Ser Pro
 1               5                  10                  15

Gly Glu Thr Ile Ser Ile Asn Cys Arg Ala Ser Lys Thr Ile Ser
                20                  25                  30

Lys Tyr Leu Ala Trp Tyr Gln Glu Lys Pro Gly Lys Thr Asn Lys
                35                  40                  45

Leu Leu Ile Tyr Ser Gly Ser Thr Leu Gln Ser Gly Ile Pro Ser
                50                  55                  60

Arg Phe Ser Gly Ser Gly Ser Gly Thr Asp Phe Thr Leu Thr Ile
                65                  70                  75

Ser Ser Leu Glu Pro Glu Asp Phe Ala Met Tyr Tyr Cys Gln Gln
                80                  85                  90

His Asn Glu Tyr Pro Leu Thr Phe Gly Thr Gly Thr Lys Leu Glu
                95                 100                 105

Leu Lys Arg (2) INFORMATION FOR SEQ ID NO: 2:

(i) SEQUENCE CHARACTERISTICS:
        (A) LENGTH: 108 amino acids
        (B) TYPE: Amino Acid
        (D) TOPOLOGY: Linear (xi) SEQUENCE DESCRIPTION: SEQ ID NO: 2:

Asp Ile Gln Met Thr Gln Ser Pro Ser Ser Leu Ser Ala Ser Val
 1               5                  10                  15

Gly Asp Arg Val Thr Ile Thr Cys Arg Ala Ser Lys Thr Ile Ser
                20                  25                  30

Lys Tyr Leu Ala Trp Tyr Gln Gln Lys Pro Gly Lys Ala Pro Lys
                35                  40                  45

Leu Leu Ile Tyr Ser Gly Ser Thr Leu Gln Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

His Asn Glu Tyr Pro Leu Thr Phe Gly Gln Gly Thr Lys Val Glu
                95                 100                 105

Ile Lys Arg (2) INFORMATION FOR SEQ ID NO: 3:

(i) SEQUENCE CHARACTERISTICS:
        (A) LENGTH: 108 amino acids
        (B) TYPE: Amino Acid
        (D) TOPOLOGY: Linear (xi) SEQUENCE DESCRIPTION: SEQ ID NO: 3:

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
                35                  40                  45

```
Leu Leu Ile Tyr Ala Ala Ser Ser Leu Glu Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                95                 100                 105

Ile Lys Arg (2) INFORMATION FOR SEQ ID NO: 4:

(i) SEQUENCE CHARACTERISTICS:
        (A) LENGTH: 121 amino acids
        (B) TYPE: Amino Acid
        (D) TOPOLOGY: Linear (xi) SEQUENCE DESCRIPTION: SEQ ID NO: 4:

Glu Val Gln Leu Gln Gln Pro Gly Ala Glu Leu Met Arg Pro Gly
 1               5                  10                  15

Ala Ser Val Lys Leu Ser Cys Lys Ala Ser Gly Tyr Ser Phe Thr
                20                  25                  30

Gly His Trp Met Asn Trp Val Arg Gln Arg Pro Gly Gln Gly Leu
                35                  40                  45

Glu Trp Ile Gly Met Ile His Pro Ser Asp Ser Glu Thr Arg Leu
                50                  55                  60

Asn Gln Lys Phe Lys Asp Lys Ala Thr Leu Thr Val Asp Lys Ser
                65                  70                  75

Ser Ser Ser Ala Tyr Met Gln Leu Ser Ser Pro Thr Ser Glu Asp
                80                  85                  90

Ser Ala Val Tyr Tyr Cys Ala Arg Gly Ile Tyr Phe Tyr Gly Thr
                95                 100                 105

Thr Tyr Phe Asp Tyr Trp Gly Gln Gly Thr Thr Leu Thr Val Ser
               110                 115                 120

Ser (2) INFORMATION FOR SEQ ID NO: 5:

(i) SEQUENCE CHARACTERISTICS:
        (A) LENGTH: 121 amino acids
        (B) TYPE: Amino Acid
        (D) TOPOLOGY: Linear (xi) SEQUENCE DESCRIPTION: SEQ ID NO: 5:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Ser Phe Thr
                20                  25                  30

Gly His Trp Met Asn Trp Val Arg Gln Ala Pro Gly Lys Gly Leu
                35                  40                  45

Glu Trp Val Gly Met Ile His Pro Ser Asp Ser Glu Thr Arg Tyr
                50                  55                  60

Asn Gln Lys Phe Lys Asp Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90
```

-continued

```
Thr Ala Val Tyr Tyr Cys Ala Arg Gly Ile Tyr Phe Tyr Gly Thr
                 95                 100                 105

Thr Tyr Phe Asp Tyr Trp Gly Gln Gly Thr Leu Val Thr Val Ser
            110                 115                 120

Ser
```

(2) INFORMATION FOR SEQ ID NO: 6:

(i) SEQUENCE CHARACTERISTICS:
        (A) LENGTH: 113 amino acids
        (B) TYPE: Amino Acid
        (D) TOPOLOGY: Linear (xi) SEQUENCE DESCRIPTION: SEQ ID NO: 6:

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu
            35                  40                  45

Glu Trp Val Ser Val Ile Ser Gly Asp Gly Gly Ser Thr Tyr Tyr
            50                  55                  60

Ala Asp Ser Val Lys Gly Arg Phe Thr Ile Ser Arg Asp Asn Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Arg Gly Phe Asp Tyr Trp Gly Gln
            95                  100                 105

Gly Thr Leu Val Thr Val Ser Ser
            110
```

(2) INFORMATION FOR SEQ ID NO: 7:

(i) SEQUENCE CHARACTERISTICS:
        (A) LENGTH: 184 amino acids
        (B) TYPE: Amino Acid
        (D) TOPOLOGY: Linear (xi) SEQUENCE DESCRIPTION: SEQ ID NO: 7:

```
Lys Gly Asn Val Asp Leu Val Phe Leu Phe Asp Gly Ser Met Ser
 1               5                  10                  15

Leu Gln Pro Asp Glu Phe Gln Lys Ile Leu Asp Phe Met Lys Asp
            20                  25                  30

Val Met Lys Lys Leu Ser Asn Thr Ser Tyr Gln Phe Ala Ala Val
            35                  40                  45

Gln Phe Ser Thr Ser Tyr Lys Thr Glu Phe Asp Phe Ser Asp Tyr
            50                  55                  60

Val Lys Arg Lys Asp Pro Asp Ala Leu Leu Lys His Val Lys His
            65                  70                  75

Met Leu Leu Leu Thr Asn Thr Phe Gly Ala Ile Asn Tyr Val Ala
            80                  85                  90

Thr Glu Val Phe Arg Glu Glu Leu Gly Ala Arg Pro Asp Ala Thr
            95                  100                 105

Lys Val Leu Ile Ile Ile Thr Asp Gly Glu Ala Thr Asp Ser Gly
            110                 115                 120

Asn Ile Asp Ala Ala Lys Asp Ile Ile Arg Tyr Ile Ile Gly Ile
            125                 130                 135
```

-continued

Gly Lys His Phe Gln Thr Lys Glu Ser Gln Glu Thr Leu His Lys
                140                 145                 150

Phe Ala Ser Lys Pro Ala Ser Glu Phe Val Lys Ile Leu Asp Thr
                155                 160                 165

Phe Glu Lys Leu Lys Asp Leu Phe Thr Glu Leu Gln Lys Lys Ile
                170                 175                 180

Tyr Val Ile Glu (2) INFORMATION FOR SEQ ID NO: 8:

(i) SEQUENCE CHARACTERISTICS:
        (A) LENGTH: 184 amino acids
        (B) TYPE: Amino Acid
        (D) TOPOLOGY: Linear (xi) SEQUENCE DESCRIPTION: SEQ ID NO: 8:

Lys Gly Asn Val Asp Leu Ile Phe Leu Phe Asp Gly Ser Met Ser
  1                 5                  10                  15

Leu Gln Pro Asp Glu Phe Gln Lys Ile Leu Asp Phe Met Lys Asp
                 20                  25                  30

Val Met Lys Lys Leu Ser Asn Thr Ser Tyr Gln Phe Ala Ala Val
                 35                  40                  45

Gln Phe Ser Thr Ser Tyr Lys Thr Glu Phe Asp Phe Ser Asp Tyr
                 50                  55                  60

Val Lys Gln Lys Asp Pro Asp Ala Leu Leu Glu His Val Lys His
                 65                  70                  75

Met Leu Leu Leu Thr Asn Thr Phe Gly Ala Ile Asn Tyr Val Ala
                 80                  85                  90

Thr Glu Val Phe Arg Glu Glu Leu Gly Ala Arg Pro Asp Ala Thr
                 95                 100                 105

Lys Val Leu Ile Ile Ile Thr Asp Gly Glu Ala Thr Asp Ser Gly
                110                 115                 120

Asn Ile Asp Ala Ala Lys Asp Ile Ile Arg Tyr Ile Ile Gly Ile
                125                 130                 135

Gly Lys His Phe Gln Thr Lys Glu Ser Gln Glu Thr Leu His Lys
                140                 145                 150

Phe Ala Ser Lys Pro Ala Ser Glu Phe Val Lys Ile Leu Asp Thr
                155                 160                 165

Phe Glu Lys Leu Lys Asp Leu Phe Thr Glu Leu Gln Lys Lys Ile
                170                 175                 180

Tyr Ala Ile Glu (2) INFORMATION FOR SEQ ID NO: 9:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 9:

Lys His Val Lys His Met Leu
  1                 5

(2) INFORMATION FOR SEQ ID NO: 10:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 10:

Gly Tyr Ser Phe Thr Gly His Trp Met Asn
 1               5                  10

(2) INFORMATION FOR SEQ ID NO: 11:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 11:

Met Ile His Pro Ser Asp Ser Glu Thr Arg Tyr Asn Gln Lys Phe
 1               5                  10                  15
Lys Asp (2) INFORMATION FOR SEQ ID NO: 12:

(i) SEQUENCE CHARACTERISTICS:
        (A) LENGTH: 12 amino acids
        (B) TYPE: Amino Acid
        (D) TOPOLOGY: Linear (xi) SEQUENCE DESCRIPTION: SEQ ID NO: 12:

Gly Ile Tyr Phe Tyr Gly Thr Thr Tyr Phe Asp Tyr
 1               5                  10

(2) INFORMATION FOR SEQ ID NO: 13:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 13:

Arg Ala Ser Lys Thr Ile Ser Lys Tyr Leu Ala
 1               5                  10

(2) INFORMATION FOR SEQ ID NO: 14:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 14:

Ser Gly Ser Thr Leu Gln Ser
 1               5

(2) INFORMATION FOR SEQ ID NO: 15:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO: 15:

Gln Gln His Asn Glu Tyr Pro Leu Thr
 1               5

(2) INFORMATION FOR SEQ ID NO: 16:

(i) SEQUENCE CHARACTERISTICS:
        (A) LENGTH: 11 amino acids
        (B) TYPE: Amino Acid (D) TOPOLOGY: Linear (xi) SEQUENCE DESCRIPTION: SEQ ID NO: 16:

Pro Lys Asn Ser Ser Met Ile Ser Asn Thr Pro
 1               5                  10

(2) INFORMATION FOR SEQ ID NO: 17:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 17:

His Gln Ser Leu Gly Thr Gln
 1               5

(2) INFORMATION FOR SEQ ID NO: 18:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 18:

His Gln Asn Leu Ser Asp Gly Lys
 1               5

(2) INFORMATION FOR SEQ ID NO: 19:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 19:

His Gln Asn Ile Ser Asp Gly Lys
 1               5

(2) INFORMATION FOR SEQ ID NO: 20:

(i) SEQUENCE CHARACTERISTICS:
        (A) LENGTH: 8 amino acids
        (B) TYPE: Amino Acid
        (D) TOPOLOGY: Linear (xi) SEQUENCE DESCRIPTION: SEQ ID NO: 20:

Val Ile Ser Ser His Leu Gly Gln
 1               5

(2) INFORMATION FOR SEQ ID NO: 21:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (xi) SEQUENCE DESCRIPTION: SEQ ID NO: 21:

CACTTTGGAT ACCGCGTCCT GCAGGT                                              26

(2) INFORMATION FOR SEQ ID NO: 22:

(i) SEQUENCE CHARACTERISTICS:
        (A) LENGTH: 26 base pairs
        (B) TYPE: Nucleic Acid
        (C) STRANDEDNESS: Single (D) TOPOLOGY: Linear (xi) SEQUENCE DESCRIPTION: SEQ ID NO: 22:

CATCCTGCAG GTCTGCCTTC AGGTCA                                          26

(2) INFORMATION FOR SEQ ID NO: 23:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 23:

Met Ile Ala Pro Ala Ser Ser Ser Thr Arg Tyr Asn Gln Lys Phe
 1               5                  10                  15

Lys Asp (2) INFORMATION FOR SEQ ID NO: 24:

(i) SEQUENCE CHARACTERISTICS:
        (A) LENGTH: 121 amino acids
        (B) TYPE: Amino Acid
        (D) TOPOLOGY: Linear (xi) SEQUENCE DESCRIPTION: SEQ ID NO: 24:

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Ser Phe Thr
                20                  25                  30

Gly His Trp Met Asn Trp Val Arg Gln Ala Pro Gly Lys Gly Leu
                35                  40                  45

Glu Trp Val Gly Met Ile Ala Pro Ala Ser Ser Ser Thr Arg Tyr
                50                  55                  60

Asn Gln Lys Phe Lys Asp Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Ile Tyr Phe Tyr Gly Thr
                95                  100                 105

Thr Tyr Phe Asp Tyr Trp Gly Gln Gly Thr Leu Val Thr Val Ser
                110                 115                 120

Ser (2) INFORMATION FOR SEQ ID NO: 25:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 25:

Gly Tyr Ser Phe Thr Gly His Trp Met Asn
 1               5                  10

(2) INFORMATION FOR SEQ ID NO: 26:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 26:

Gly Tyr Ala Phe Ala Gly Ala Trp Met Asn
1               5                   10

(2) INFORMATION FOR SEQ ID NO: 27:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 27:

Gly Tyr Ala Phe Thr Gly His Trp Met Asn
1               5                   10

(2) INFORMATION FOR SEQ ID NO: 28:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 28:

Gly Tyr Ser Phe Ala Gly His Trp Met Asn
1               5                   10

(2) INFORMATION FOR SEQ ID NO: 29:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 29:

Gly Tyr Ser Phe Thr Ala His Trp Met Asn
1               5                   10

(2) INFORMATION FOR SEQ ID NO: 30:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 30:

Gly Tyr Ser Phe Thr Gly Ala Trp Met Asn
1               5                   10

(2) INFORMATION FOR SEQ ID NO: 31:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 31:

Gly Tyr Ser Phe Thr Gly His Ala Met Asn
1               5                   10

(2) INFORMATION FOR SEQ ID NO: 32:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 32:

Met Ile His Pro Ser Asp Ser Glu Thr Arg Tyr Asn Gln Lys Phe
1               5                   10                  15

Lys Asp (2) INFORMATION FOR SEQ ID NO: 33:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 33:

Met Ile Ala Pro Ala Asp Ala Glu Thr Arg Tyr Asn Gln Lys Phe
1               5                   10                  15

Lys Asp (2) INFORMATION FOR SEQ ID NO: 34:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 34:

Met Ile His Pro Ser Ala Ser Ala Thr Ala Tyr Asn Gln Lys Phe
1               5                   10                  15

Lys Asp (2) INFORMATION FOR SEQ ID NO: 35:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 35:

Met Ile Ala Pro Ala Asp Ser Glu Thr Arg Tyr Asn Gln Lys Phe
1               5                   10                  15

Lys Asp (2) INFORMATION FOR SEQ ID NO: 36:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 36:

Met Ile His Pro Ala Asp Ala Glu Thr Arg Tyr Asn Gln Lys Phe
1               5                   10                  15

Lys Asp (2) INFORMATION FOR SEQ ID NO: 37:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 37:

Met Ile Ala Pro Ser Asp Ala Glu Thr Arg Tyr Asn Gln Lys Phe
1               5                   10                  15

Lys Asp (2) INFORMATION FOR SEQ ID NO: 38:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 38:

Met Ile Ala Pro Ser Asp Ser Glu Thr Arg Tyr Asn Gln Lys Phe
1              5                 10             15

Lys Asp (2) INFORMATION FOR SEQ ID NO: 39:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 39:

Met Ile Ser Pro Ser Asp Ser Glu Thr Arg Tyr Asn Gln Lys Phe
1              5                 10             15

Lys Asp (2) INFORMATION FOR SEQ ID NO: 40:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 40:

Met Ile His Pro Ala Asp Ser Glu Thr Arg Tyr Asn Gln Lys Phe
1              5                 10             15

Lys Asp (2) INFORMATION FOR SEQ ID NO: 41:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 41:

Met Ile His Pro Ser Ala Ser Glu Thr Arg Tyr Asn Gln Lys Phe
1              5                 10             15

Lys Asp (2) INFORMATION FOR SEQ ID NO: 42:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 42:

Met Ile His Pro Ser Asp Ala Glu Thr Arg Tyr Asn Gln Lys Phe
1              5                 10             15

Lys Asp (2) INFORMATION FOR SEQ ID NO: 43:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 43:

Met Ile His Pro Ser Asp Asn Glu Thr Arg Tyr Asn Gln Lys Phe
 1               5                  10                  15

Lys Asp (2) INFORMATION FOR SEQ ID NO: 44:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 44:

Met Ile His Pro Ser Asp Gln Glu Thr Arg Tyr Asn Gln Lys Phe
 1               5                  10                  15

Lys Asp (2) INFORMATION FOR SEQ ID NO: 45:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 45:

Met Ile His Pro Ser Asp Ser Ala Thr Arg Tyr Asn Gln Lys Phe
 1               5                  10                  15

Lys Asp (2) INFORMATION FOR SEQ ID NO: 46:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 46:

Met Ile His Pro Ser Asp Ser Glu Thr Ala Tyr Asn Gln Lys Phe
 1               5                  10                  15

Lys Asp (2) INFORMATION FOR SEQ ID NO: 47:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 47:

Met Ile His Pro Ser Asp Ser Glu Thr Arg Tyr Asn Ala Lys Phe
 1               5                  10                  15

Lys Asp (2) INFORMATION FOR SEQ ID NO: 48:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 48:

Met Ile His Pro Ser Asp Ser Glu Thr Arg Tyr Asn Gln Ala Phe
 1               5                  10                  15

Lys Asp (2) INFORMATION FOR SEQ ID NO: 49:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 49:

Met Ile His Pro Ser Asp Ser Glu Thr Arg Tyr Asn Gln Lys Phe
 1               5                  10                  15

Ala Asp (2) INFORMATION FOR SEQ ID NO: 50:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 50:

Met Ile His Pro Ser Asp Ser Glu Thr Arg Tyr Asn Gln Lys Phe
 1               5                  10                  15

Lys Ala (2) INFORMATION FOR SEQ ID NO: 51:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 51:

Gly Ile Tyr Phe Tyr Gly Thr Thr Tyr Phe Asp
 1               5                  10

(2) INFORMATION FOR SEQ ID NO: 52:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 52:

Gly Ile Ala Phe Ala Gly Thr Thr Tyr Phe Asp
 1               5                  10

(2) INFORMATION FOR SEQ ID NO: 53:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 53:

Gly Ile Tyr Phe Tyr Gly Ala Ala Ala Phe Asp
 1               5                  10

(2) INFORMATION FOR SEQ ID NO: 54:

(i) SEQUENCE CHARACTERISTICS:
    (A) LENGTH: 11 amino acids
    (B) TYPE: Amino Acid
    (D) TOPOLOGY: Linear (xi) SEQUENCE DESCRIPTION: SEQ ID NO: 54:

Gly Ile Ala Phe Tyr Gly Thr Thr Tyr Phe Asp
 1               5                   10

(2) INFORMATION FOR SEQ ID NO: 55:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 55:

Gly Ile Tyr Phe Ala Gly Thr Thr Tyr Phe Asp
 1               5                   10

(2) INFORMATION FOR SEQ ID NO: 56:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 56:

Gly Ile Tyr Phe Tyr Gly Ala Thr Tyr Phe Asp
 1               5                   10

(2) INFORMATION FOR SEQ ID NO: 57:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 57:

Gly Ile Tyr Phe Tyr Gly Thr Ala Tyr Phe Asp
 1               5                   10

(2) INFORMATION FOR SEQ ID NO: 58:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 58:

Gly Ile Tyr Phe Tyr Gly Thr Thr Ala Phe Asp
 1               5                   10

(2) INFORMATION FOR SEQ ID NO: 59:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 59:

Arg Ala Ser Lys Thr Ile Ser Lys Tyr Leu Ala
 1               5                   10

(2) INFORMATION FOR SEQ ID NO: 60:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 60:

Arg Ala Ser Ala Ala Ile Ala Ala Tyr Leu Ala
 1               5                   10

(2) INFORMATION FOR SEQ ID NO: 61:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 61:

Ser Gly Ser Thr Leu Gln Ser
 1               5

(2) INFORMATION FOR SEQ ID NO: 62:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 62:

Ala Gly Ala Ala Leu Gln Ser
 1               5

(2) INFORMATION FOR SEQ ID NO: 63:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 63:

Ala Gly Ser Thr Leu Gln Ser
 1               5

(2) INFORMATION FOR SEQ ID NO: 64:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 64:

Ser Gly Ala Thr Leu Gln Ser
 1               5

(2) INFORMATION FOR SEQ ID NO: 65:

(i) SEQUENCE CHARACTERISTICS:
        (A) LENGTH: 7 amino acids
        (B) TYPE: Amino Acid
        (D) TOPOLOGY: Linear (xi) SEQUENCE DESCRIPTION: SEQ ID NO: 65:

Ser Gly Ser Ala Leu Gln Ser
 1               5

(2) INFORMATION FOR SEQ ID NO: 66:

(i) SEQUENCE CHARACTERISTICS:

(A) LENGTH: 9 amino acids
                (B) TYPE: Amino Acid
                (D) TOPOLOGY: Linear (xi) SEQUENCE DESCRIPTION: SEQ ID NO: 66:

Gln Gln His Asn Glu Tyr Pro Leu Thr
     1               5

(2) INFORMATION FOR SEQ ID NO: 67:

(i) SEQUENCE CHARACTERISTICS:
                (A) LENGTH: 9 amino acids
                (B) TYPE: Amino Acid
                (D) TOPOLOGY: Linear (xi) SEQUENCE DESCRIPTION: SEQ ID NO: 67:

Gln Gln His Ala Ala Ala Pro Leu Thr
     1               5

(2) INFORMATION FOR SEQ ID NO: 68:

(i) SEQUENCE CHARACTERISTICS:
                (A) LENGTH: 9 amino acids
                (B) TYPE: Amino Acid
                (D) TOPOLOGY: Linear (xi) SEQUENCE DESCRIPTION: SEQ ID NO: 68:

Gln Gln Ala Asn Glu Tyr Pro Leu Thr
     1               5

(2) INFORMATION FOR SEQ ID NO: 69:

(i) SEQUENCE CHARACTERISTICS:
                (A) LENGTH: 9 amino acids
                (B) TYPE: Amino Acid
                (D) TOPOLOGY: Linear (xi) SEQUENCE DESCRIPTION: SEQ ID NO: 69:

Gln Gln His Ala Glu Tyr Pro Leu Thr
     1               5

(2) INFORMATION FOR SEQ ID NO: 70:

(i) SEQUENCE CHARACTERISTICS:
                (A) LENGTH: 9 amino acids
                (B) TYPE: Amino Acid
                (D) TOPOLOGY: Linear (xi) SEQUENCE DESCRIPTION: SEQ ID NO: 70:

Gln Gln His Asn Ala Tyr Pro Leu Thr
     1               5

(2) INFORMATION FOR SEQ ID NO: 71:

(i) SEQUENCE CHARACTERISTICS:
                (A) LENGTH: 9 amino acids
                (B) TYPE: Amino Acid
                (D) TOPOLOGY: Linear (xi) SEQUENCE DESCRIPTION: SEQ ID NO: 71:

Gln Gln His Asn Glu Ala Pro Leu Thr
     1               5

US 6,703,018 B2

METHOD OF TREATMENT USING HUMANIZED ANTI-CD11A ANTIBODIES

This is a divisional application claiming priority under 35 U.S.C. §120 to application Ser. No. 09/420,745 filed Oct. 20, 1999, which application is now abandoned, which is a continuation of application Ser. No. 08/974,899, filed Nov. 20, 1997, now U.S. Pat. No. 6,037,454, which claims the benefit under 35 U.S.C. §119(e) to provisional application No. 60/031,971, filed Nov. 27, 1996, which applications are incorporated herein by reference.

BACKGROUND OF THE INVENTION

1. Field of the Invention

This invention relates generally to humanized anti-CD11a antibodies.

2. Description of Related Art

Lymphocyte function-associated antigen 1 (LFA-1; CD11a/CD18) is involved in leukocyte adhesion during cellular interactions essential for immunologic responses and inflammation (Larson et al., *Immunol. Rev.* 114:181–217 (1990)). LFA-1 is a member of the β2 integrin family and consists of a unique α subunit, CD11a, and a β subunit, CD18, common to other β2 integrin receptors Mac-1 and p150,95. The ligands of LFA-1 include intercellular adhesion molecule-1, ICAM-1, expressed on leukocytes, endothelium, and dermal fibroblasts (Dustin et al., *J. Immunol.* 137:245–254 (1986)), ICAM-2 expressed on resting endothelium and lymphocytes (de Fougerolles et al., *J. Exp. Med.* 174:253–267 (1991)), and ICAM-3 expressed on monocytes and resting lymphocytes (de Fougerolles et al., *J. Exp. Med.* 179:619–629 (1994)).

Monoclonal antibodies (MAbs) against LFA-1 and the ICAMs have been shown, in vitro, to inhibit several T cell-dependent immune functions including T cell activation (Kuypers et al., *Res. Immunol.* 140:461(1989)), T cell-dependent B cell proliferation (Fischer et al., *J. Immunol.* 136:3198–3203 (1986)), target cell lysis (Krensky et al., *J. Immunol.* 131:611–616 (1983)), and adhesion of T cells to vascular endothelium (Lo et al., *J. Immunol.* 143:3325–3329 (1989)). In mice, anti-CD11a MAbs induce tolerance to protein antigens (Tanaka et al., *Eur. J. Immunol.* 25:1555–1558 (1995)) and prolong survival of cardiac (Cavazzana-Calvo et al., *Transplantation* 59:1576–1582 (1995); Nakakura et al., *Transplantation* 55:412–417 (1993)), bone marrow (Cavazzana-Calvo et al., *Transplantation* 59:1576–1582 (1995); van Dijken et al., *Transplantation* 49:882–886 (1990)), corneal (He et al., *Invest. Opthamol. Vis. Sci.* 35:3218–3225 (1994)), islet (Nishihara et al., *Transplantation Proc.* 27:372 (1995)) and thyroid (Talento et al., *Transplantation* 55:418–422 (1993)) allografts.

In humans, anti-CD11a MAbs prevent graft failure after bone marrow transplantation (Fischer et al., *Blood* 77:249–256 (1991); Stoppa et al., *Transplant Intl.* 4:3–7 (1991)) and preliminary clinical studies of renal allografts treated prophylactically with anti-CD11a MAb, in addition to corticosteroids and azathioprine, are promising (Hourmant et al., *Transplantation* 58:377–380 (1994)). Current therapies against graft rejection include use of OKT3, a murine anti-human CD3 MAb, and cyclosporin A. OKT3 therapy is effective but has several undesirable side effects; its use results in the release of numerous cytokines including tumor necrosis factor-α, interferon-γ, interleukin-2, and interleukin-6, resulting in fever, chills and gastrointestinal distress (for a review see Parlevliet et al., *Transplant Intl.* 5:234–246 (1992); Dantal et al., *Curr. Opin. Immunol.* 3:740–747 (1991)). Cyclosporin A is effective but also has serious side effects (for a review see Barry, *Drugs*, 44:554–566 (1992)).

SUMMARY OF THE INVENTION

The instant invention provides humanized anti-CD11a antibodies. Preferred antibodies bind to the I-domain of human CD11a (e.g. to "epitope MHM24" as herein defined) and/or bind CD11a with an affinity of about $1 \times 10^8 M$ or stronger. In preferred embodiments, the antibody has an IC50 (nM) value of no more than about 1 nM for preventing adhesion of Jurkat cells to normal human epidermal keratinocytes expressing ICAM-1. Preferred humanized antibodies are those which have an IC50 (nM) value of no more than about 1 nM in the mixed lymphocyte response (MLR) assay. This IC50 for a humanized antibody in the MLR assay is significantly better than that that for murine MAb 25.3, which has been previously tested in vivo (Fischer et al., *Blood* 77:249–256 (1991); Stoppa et al., *Transplant Intl.* 4:3–7 (1991); Hourmant et al., *Transplantation* 58:377–380 (1994)).

The humanized anti-CD11a antibody may have a heavy chain variable region comprising the amino acid sequence of CDR1 (GYSFTGHWMN; SEQ ID NO:10) and/or CDR2 (MIHPSDSETRYNQKFKD; SEQ ID NO:11) and/or CDR3 (GIYFYGTTYFDY; SEQ ID NO:12) of humanized antibody MHM24 F(ab)-8 in FIG. 1 and/or a light chain variable region comprising the amino acid sequence of CDR1 (RASKTISKYLA; SEQ ID NO:13) and/or CDR2 (SGSTLQS; SEQ ID NO:14) and/or CDR3 (QQHNEYPLT; SEQ ID NO:15) of humanized antibody MHM24 F(ab)-8 in FIG. 1. In other embodiments, the antibody comprises an amino acid sequence variant of one or more of the CDRs of humanized MHM24 antibody F(ab)-8, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally having a binding affinity for human CD11a which is no more than about $1 \times 10^{-8} M$.

In preferred embodiments, the humanized antibody includes a light chain variable region comprising the amino acid sequence of SEQ ID NO:2 and/or a heavy chain variable region comprising the amino acid sequence of SEQ ID NO:5 of humanized antibody MHM24 F(ab)-8 in FIG. 1 and/or amino acid sequence variants thereof.

As described herein, it has been possible to reengineer a humanized antibody that bound human CD11a antigen, but not significantly to rhesus CD11a antigen, so as to confer an ability to bind to rhesus CD11a (i.e. a "rhesusized" antibody). In this embodiment, the antibody which binds rhesus CD11a may, for example, comprise the the CDR2 amino acid sequence in SEQ ID NO:23. The other CDRs may be the same as those for humanized MHM24 antibody F(ab)-8. Thus, the antibody may comprise the amino acid sequence of the "rhesusized" heavy chain in SEQ ID NO:24, optionally combined with a light chain comprising the amino acid sequence in SEQ ID NO:2.

Various forms of the antibody are contemplated herein. For example, the anti-CD11a antibody may be a full length antibody (e.g. having a human immunoglobulin constant region) or an antibody fragment (e.g. a F(ab')$_2$). Furthermore, the antibody may be labeled with a detectable label, immobilized on a solid phase and/or conjugated with a heterologous compound (such as a cytotoxic agent).

Diagnostic and therapeutic uses for the antibody are contemplated. In one diagnostic application, the invention provides a method for determining the presence of CD11a protein comprising exposing a sample suspected of containing the CD11a protein to the anti-CD11a antibody and determining binding of the antibody to the sample. For this use, the invention provides a kit comprising the antibody and instructions for using the antibody to detect the CD11a protein.

The invention further provides: isolated nucleic acid encoding the antibody; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium).

The invention also provides a composition comprising the humanized anti-CD11a antibody and a pharmaceutically acceptable carrier or diluent. This composition for therapeutic use is sterile and may be lyophilized. The invention further provides a method for treating a mammal suffering from a LFA-1 mediated disorder, comprising administering a pharmaceutically effective amount of the humanized anti-CD11a antibody to the mammal. For such therapeutic uses, other immunosuppressive agents or adhesion molecule antagonists (e.g. another LFA-1 antagonist or a VLA-4 antagonist) may be co-administered to the mammal either before, after, or simultaneously with, the humanized anti-CD11a antibody.

BRIEF DESCRIPTION OF THE DRAWINGS

FIG. 1A shows the amino acid sequences of murine MHM24 light chain (SEQ ID NO:1), humanized MHM24 F(ab)-8 light chain (SEQ ID NO:2), human consensus sequences of light chain subgroup kl (humkl) (SEQ ID NO:3).

FIG. 1B shows the amino acid sequences of murine MHM24 heavy chain (SEQ ID NO:4), humanized MHM24 F(ab)-8 heavy chain(SEQ ID NO:5), human consensus sequences of heavy chain subgroup III (humIII) (SEQ ID NO:6) and "rhesusized" antibody mutant heavy chain of the Example (SEQ ID NO:24).

In FIGS. 1A and 1B, hypervariable regions based on sequence hypervariability (Kabat et al., *Sequences of Proteins of Immunological Interest.* 5th Ed. Public Health Service, National Institutes of Health, Bethesda, Md. (1991)) are enclosed within brackets and hypervariable loops based on structure of F(ab)-antigen complexes (Chothia et al., *Nature* 342:8767 (1989)) are in italics. Residue numbering is according to Kabat et al., with insertions shown as a, b, and c.

FIG. 2 shows sequences of human CD11a I-domain (SEQ ID NO:7) and rhesus CD11a I-domain (SEQ ID NO:8). β-strands and α-helices are underlined and labeled according to Qu et al., *Proc. Natl. Acad. Sci.* 92:10277–10281 (1995). The rhesus I-domain sequence (rhCD11a) shows only the four differences from human I-domain. The binding epitope for the MHM24 MAb (SEQ ID NO:9) is shown in bold (Champe et al., *J. Biol. Chem.* 270:1388–1394 (1995)).

FIG. 3 depicts inhibition of human Jurkat T-cells to normal human keratinocytes by murine MHM24 (filled circles), chimeric MHM24 (open triangles), humanized MHM24 (HuIgG1) (filled squares), and a human IgG1 isotype control (+). Percent binding measured by fluorescence of labeled Jurkat cells.

FIGS. 4A–4C show inhibition of binding of rhesus lymphocytes to normal human keratinocytes (FIG. 4A), rhesus lymphocytes to recombinant human ICAM-1 coated on plates (FIG. 4B), and rhesus/human CD11a chimera-transfected 293 cells to normal human keratinocytes (FIG. 4C). Inhibition by rhesus-binding MHM24 (RhIgG1) (filled squares), anti-CD18 MHM23 (filled circles), a human IgG1 isotype control (+) (FIGS. 4A and 4C), and a murine IgG1 isotype control (+) (FIG. 4B). Percent binding measured by fluorescence of labeled lymphocytes (FIGS. 4A and B) or labeled 293 cells (FIG. 4C).

FIG. 5 shows human mixed lymphocyte response assy (MLR) is blocked by murine MHM24 (filled circles), humanized MHM24 (HuIgG1) (filled squares), and a humanized isotype IgG1 control (filled diamond). Percent stimulation index (%SI) is the ratio of the response at a given MAb concentration to the maximal response with no MAb present. Data is representative of multiple assays using at least two different stimulator/responder pairs.

DETAILED DESCRIPTION OF THE PREFERRED EMBODIMENTS

I. Definitions

Unless indicated otherwise, the term "CD11a" when used herein refers to the alpha subunit of LFA-1 from any mammal, but preferably from a human. The CD11a may be isolated from a natural source of the molecule or may be produced by synthetic means (e.g., using recombinant DNA technology.) The amino acid sequence for human CD11a is described in EP 362 526B1, for example.

The term "I-domain" of CD11a refers to the region of this molecule delineated in Champe et al., *J. Biol. Chem.* 270:1388–1394 (1995) and/or Qu et al. *Proc. Natl. Acad. Sci.* 92:10277–10281 (1995). The amino acid sequences of human CD11a I-domain (SEQ ID NO:7) and rhesus CD11a I-domain (SEQ ID NO:8) are depicted in FIG. 2 herein.

The term "epitope MHM24" when used herein, unless indicated otherwise, refers to the region in the I-domain of human CD11a to which the MHM24 antibody (see Example below) binds. This epitope comprises the amino acid sequence of SEQ ID NO:9 and, optionally, other amino acid residues of CD11a and/or CD18.

The term "LFA-1-mediated disorder" refers to a pathological state caused by cell adherence interactions involving the LFA-1 receptor on lymphocytes. Examples of such disorders include T cell inflammatory responses such as inflammatory skin diseases including psoriasis; responses associated with inflammatory bowel disease (such as Crohn's disease and ulcerative colitis); adult respiratory distress syndrome; dermatitis; meningitis; encephalitis; uveitis; allergic conditions such as eczema and asthma; conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; chronic obstructive pulmonary disease (COPD); bronchitis; insulinitis; rhinitis; urticaria; glomerulonephritis; diseases involving leukocyte diapedesis; CNS inflammatory disorder; multiple organ injury syndrome is secondary to septicaemia or trauma; autoimmune hemolytic anemia; myethemia gravis; antigen-antibody complex mediated diseases; nephrotic syndrome; malignancies (e.g., B-cell malignancies such as chronic lymphocytic leukemia or hairy cell leukemia); all types of transplantations, including graft vs. host or host vs. graft disease; HIV and rhinovirus infection; pulmonary fibrosis; invasion of tumor cells into secondary organs etc.

The term "immunosuppressive agent" as used herein for adjunct therapy refers to substances that act to suppress or mask the immune system of the host into which the graft is being transplanted. This would include substances that suppress cytokine production, downregulate or suppress self-antigen expression, or mask the MHC antigens. Examples of such agents include 2-amino-6-aryl-5-substituted pyrimidines (see U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-$\gamma$, -$\beta$, or -$\alpha$ antibodies; anti-tumor necrosis factors antibodies; anti-tumor necrosis factor-s antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-$\beta$; streptodomase; RNA or DNA from the host; FK506; RS-61443; deoxyspergualin; rapamycin; T-cell receptor (U.S. Pat. No. 5,114,721); T-cell receptor fragments (Offner et al., *Science* 251:430–432 (1991); WO 90/11294; and WO 91/01133); and T cell receptor antibodies (EP 340,109) such as T10B9. These agents are administered at the same time or at separate times from the CD11a antibody, and are used at the same or lesser dosages than as set forth in the art. The preferred adjunct immunosuppressive agent will depend on many factors, including the type of disorder being treated including the type of transplantation being performed, as well as the patient's history, but a general overall preference is that the agent be selected from cyclosporin A, a glucocorticosteroid (most preferably prednisone or methylprednisolone), OKT-3 monoclonal antibody, azathioprine, bromocryptine, heterologous anti-lymphocyte globulin, or a mixture thereof.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

The term "graft" as used herein refers to biological material derived from a donor for transplantation into a recipient. Grafts include such diverse material as, for example, isolated cells such as islet cells and neural-derived cells (e.g. schwann cells), tissue such as the amniotic membrane of a newborn, bone marrow, hematopoietic precursor cells, and organs such as skin, heart, liver, spleen, pancreas, thyroid lobe, lung, kidney, tubular organs (e.g., intestine, blood vessels, or esophagus), etc. The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. Preferably the graft is bone marrow or an organ such as heart and the donor of the graft and the host are matched for HLA class II antigens.

The term "donor" as used herein refers to the mammalian species, dead or alive, from which the graft is derived. Preferably, the donor is human. Human donors are preferably volunteer blood-related donors that are normal on physical examination and of the same major ABO blood group, because crossing major blood group barriers possibly prejudices survival of the allograft. It is, however, possible to transplant, for example, a kidney of a type O donor into an A, B or AB recipient.

The term "transplant" and variations thereof refers to the insertion of a graft into a host, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, such as a baboon heart transplanted into a human recipient host, and including animals from phylogenically widely separated species, for example, a pig heart valve, or animal beta islet cells or neuronal cells transplanted into a human host.

"Increasing tolerance of a transplanted graft" by a host refers to prolonging the survival of a graft in a host in which it is transplanted, i.e., suppressing the immune system of the host so that it will better tolerate a foreign transplant.

"Intermittent" or "periodic" dosing is a dosing that is continuous for a certain period of time and is at regular intervals that are preferably separated by more than one day.

"Selective tolerance" of the disorder refers to a tolerance by the host's immune system for the specific agent causing the disorder, but retaining the ability of the host to reject a second allogeneic or xenogeneic graft. Preferably, the tolerance is such that the immune system is left otherwise intact.

The term "LFA-1 antagonist" refers to a molecule that acts as a competitive inhibitor of the LFA-1 interaction with ICAM-1. Examples of such molecules include antibodies directed against either CD11a (e.g., the humanized anti-CD11a antibodies described herein) or CD18 or both, antibodies to ICAM-1, and other molecules such as peptides (e.g., peptidomimetic antagonists).

The term "VLA-4 antagonist" refers to a molecule that acts as a competitive inhibitor of the VLA-4 interaction with VCAM. Examples of such molecules include antibodies directed against either VLA-4 or VCAM and other molecules (e.g., peptidomimetic antagonists).

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624–628 (1991) and Marks et al., J. Mol. Biol. 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851–6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26–32 (L1), 50–52 (L2) and 91–96 (L3) in the light chain variable domain and 26–32 (H1), 53–55 (H2) and 96–101 (H3) in the heavy chain variable domain; Chothia and Lesk J. Mol. Biol. 196:901–917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522–525 (1986); Reichmann et al., Nature 332:323–329 (1988); and Presta, Curr. Op. Struct. Biol. 2:593–596 (1992).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269–315 (1994).

The term "diabodies" refers to small antibody fragments with two antigen-binding sites, which fragments comprise a heavy chain variable domain ($V_H$ connected to a light chain variable domain ($V_L$) in the same polypeptide chain ($V_H$–$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90:6444–6448 (1993).

The expression "linear antibodies" when used throughout this application refers to the antibodies described in Zapata et al. Protein Eng. 8(10):1057–1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to the anti-CD11a antibody fused to an "epitope tag". The epitope tag polypeptide has enough residues to provide an epitope against which an antibody thereagainst can be made, yet is short enough such that it does not interfere with activity of the CD11a antibody. The epitope tag preferably is sufficiently unique so that the antibody thereagainst does not substantially cross-react with other epitopes. Suitable tag polypeptides generally have at least 6 amino acid residues and usually between about 8–50 amino acid residues (preferably between about 9–30 residues). Examples include the flu HA tag polypeptide and its antibody 12CA5 (Field et al. *Mol. Cell. Biol.* 8:2159–2165 (1988)); the c-myc tag and the 8F9, 3C7, 6E10, G4, B7 and 9E10 antibodies thereto (Evan et al., *Mol. Cell. Biol.* 5(12):3610–3616 (1985)); and the Herpes Simplex virus glycoprotein D (gD) tag and its antibody (Paborsky et al., *Protein Engineering* 3(6) :547–553 (1990)). In certain embodiments, the epitope tag is a "salvage receptor binding epitope". As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan and other related nitrogen mustards.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375–382, 615th Meeting Belfast (1986) and Stella et al., "Prodrugs: A Chemical Approach to Targeted Drug Delivery," *Directed Drug Delivery*, Borchardt et al., (ed.), pp. 247–267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-CD11a antibodies disclosed herein and, optionally, a chemotherapeutic agent) to a mammal. The components of the liposome are commonly arranged in a bilayer formation, similar to the lipid arrangement of biological membranes.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

II. Modes for Carrying out the Invention

A. Antibody Preparation

A method for humanizing a nonhuman CD11a antibody is described in the Example below. In order to humanize an anti-CD11a antibody, the nonhuman antibody starting material is prepared. Exemplary techniques for generating such antibodies will be described in the following sections.

(i) Antigen Preparation

The CD11a antigen to be used for production of antibodies may be, e.g., a soluble form of the extracellular domain of CD11a or other fragment of CD11a (e.g. a CD11a fragment comprising the "MHM24 epitope", such as CD11a I-domain fragment). Alternatively, cells expressing CD11a at their cell surface can be used to generate antibodies. Such cells can be transformed to express CD11a and, optionally, CD18 or may be other naturally occurring cells (e.g. human lymphoblastoid cells, see Hildreth et al. *Eur. J. Immunol.* 13:202–208 (1983)) or Jurkat cells (see Example below). Other forms of CD11a useful for generating antibodies will be apparent to those skilled in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

(iv) Humanization and Amino Acid Sequence Variants

The Example below describes a procedure for humanization of an anti-CD11a antibody. In certain embodiments, it may be desirable to generate amino acid sequence variants of the humanized antibody, particularly where these improve the binding affinity or other biological properties of the humanized antibody.

Amino acid sequence variants of humanized anti-CD11a antibody are prepared by introducing appropriate nucleotide changes into the humanized anti-CD11a antibody DNA, or by peptide synthesis. Such variants include, for example, deletions from, and/or insertions into and/or substitutions of, residues within the amino acid sequences shown for the humanized anti-CD11a F(ab)-8 (e.g. as in SEQ ID NO's 2 & 5). Any combination of deletion, insertion, and substitution is made to arrive at the final construct, provided that the final construct possesses the desired characteristics. The amino acid changes also may alter post-translational processes of the humanized anti-CD11a antibody, such as changing the number or position of glycosylation sites.

A useful method for identification of certain residues or regions of the humanized anti-CD11a antibody polypeptide that are preferred locations for mutagenesis is called "alanine scanning mutagenesis," as described by Cunningham and Wells Science, 244:1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with CD11a antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed humanized anti-CD11a antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-CD11a antibody with an N-terminal methionyl residue or the antibody fused to an epitope tag. Other insertional variants of the humanized anti-CD11a antibody molecule include the fusion to the N- or C-terminus of humanized anti-CD11a antibody of an enzyme or a polypeptide which increases the serum half-life of the antibody (see below).

Another type of variant is an amino acid substitution variant. These variants have at least one amino acid residue in the humanized anti-CD11a antibody molecule removed and a different residue inserted in its place. The sites of greatest interest for substitutional mutagenesis include the hypervariable loops, but FR alterations are also contemplated. Table IV in the Example below provides guidance as to hypervariable region residues which can be altered. Hypervariable region residues or FR residues involved in antigen binding are generally substituted in a relatively conservative manner. Such conservative substitutions are shown in Table I under the heading of "preferred substitutions". If such substitutions result in a change in biological activity, then more substantial changes, denominated "exemplary substitutions" in Table I, or as further described below in reference to amino acid classes, are introduced and the products screened.

TABLE I

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |

TABLE I-continued

| Original Residue | Exemplary Substitutions | Preferred Substitutions |
| --- | --- | --- |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the humanized anti-CD11a antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of humanized anti-CD11a antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-CD11a antibody.

Ordinarily, amino acid sequence variants of the humanized anti-CD11a antibody will have an amino acid sequence having at least 75% amino acid sequence identity with the original humanized antibody amino acid sequences of either the heavy or the light chain (e.g. as in SEQ ID NO:2 or 5), more preferably at least 80%, more preferably at least 85%, more preferably at least 90%, and most preferably at least 95%. Identity or homology with respect to this sequence is defined herein as the percentage of amino acid residues in the candidate sequence that are identical with the humanized anti-CD11a residues, after aligning the sequences and introducing gaps, if necessary, to achieve the maximum percent sequence identity, and not considering any conservative substitutions (as defined in Table I above) as part of the sequence identity. None of N-terminal, C-terminal, or internal extensions, deletions, or insertions into the antibody sequence shall be construed as affecting sequence identity or homology.

(v) Screening for Biological Properties

Antibodies having the characteristics identified herein as being desirable in a humanized anti-CD11a antibody are screened for.

To screen for antibodies which bind to the epitope on CD11a bound by an antibody of interest (e.g., those which block binding of the MHM24 antibody to CD11a), a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388–1394 (1995), can be performed to determine whether the antibody binds an epitope of interest.

Antibody affinities (e.g. for human CD11a or rhesus CD11a) may be determined by saturation binding using either peripheral blood mononuclear cells or rhesus leukocytes as described in the Example below. According to this method for determining antibody affinity, lymphocytes or rhesus leukocytes are added to the plates in a volume of 170 $\mu$l per well and plates are incubated for 2 hr at room. After incubation, cells are harvested and washed 10 times. Samples are then counted. Data is transformed from counts per minute to nanomolarity and four-parameter curve-fitting of saturation plots (bound versus total) are then performed to determine $K_d$ (app) values. Preferred humanized antibodies are those which bind human CD11a with a $K_d$ value of no more than about $1\times10^{-7}$; preferably no more than about $1\times10^{-8}$; more preferably no more than about $1\times10^{-9}$; and most preferably no more than about $2\times10^{-10}$.

It is also desirable to select humanized antibodies which have beneficial anti-adhesion properties in the "keratinocyte monolayer adhesion assay". Preferred antibodies are those which have an IC50 (nM) value of no more than about 250 nM; preferably no more than about 100 nM; more preferably no more than about 1 nM and most preferably no more than about 0.5 nM for preventing adhesion of Jurkat cells to normal human epidermal keratinocytes expressing ICAM-1. According to this assay, normal human epidermal keratinocytes are removed from culture flasks and resuspended in lymphocyte assay medium at a concentration of $5\times10^5$ viable cells/ml. Aliquots of 0.1 ml/well are then cultured overnight in flat-bottom 96-well plates; appropriate wells are stimulated by addition of interferon-gamma at 100 units/well. Jurkat clone E6-1 cells are labeled, washed, resuspended to $1\times10^6$ cells/ml, and incubated with 2-fold serial dilutions starting at 500 ng/ml antibody at 4° C. for 30 min. After removal of medium from the keratinocyte monolayer, 0.1 ml/well of labeled cells are added and incubated at 37° C. for 1 h. The wells are washed to remove non-attached cells and fluorescence is measured.

Desirable humanized anti-CD11a antibodies are those which have an IC50 (nM) value of no more than about 100 nM; preferably no more than about 50 nM; more preferably no more than about 5 nM and most preferably no more than about 1 nM in the mixed lymphocyte response (MLR) assay, using human lymphocytes. For both human and rhesus MLR, peripheral blood lymphocytes from two unrelated donors are isolated from whole, heparinized blood and are resuspended to a concentration of $3\times10^6$ cells/ml in RPMI 1640 (GIBCO) with additives as described in the Example below. The stimulator cells are made unresponsive by irradiation. Responder cells at a concentration of $1.5\times10^5$ cells per well are co-cultured with an equal number of stimulator cells in 96-well, flat-bottom plates. Two-fold serial dilutions of antibody starting at a concentration of 10 nM are added to the cultures to give a total volume of 200 $\mu$l/well. The cultures are incubated at 37° C. in 5% $CO_2$ for 5 days and then pulsed with 1 $\mu$Ci/well of [$^3$H]thymidine for 16 h and [$^3$H]thymidine incorporation is measured.

(vi) Antibody Fragments

In certain embodiments, the humanized CD11a antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107–117 (1992) and Brennan et al., *Science* 229:81 (1985)). However, these fragments can now be produced directly by recombinant host cells. For example, Fab'-SH fragments can be directly recovered from *E. coli* and chemically coupled to form F(ab')$_2$ fragments (Carter et al., *Bio/Technology* 10:163–167 (1992)). According to another approach, F(ab')$_2$ fragments can be isolated directly from recombinant host cell culture. Other techniques for the production of antibody fragments will be apparent to the skilled practitioner.

(vii) Multispecific Antibodies

In some embodiments, it may be desirable to generate multispecific (e.g. bispecific) humanized CD11a antibodies having binding specificities for at least two different epitopes. Exemplary bispecific antibodies may bind to two different epitopes of the CD11a protein. Alternatively, an anti-CD11a arm may be combined with an arm which binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the CD11a-expressing cell. Bispecific antibodies may also be used to localize cytotoxic agents to cells which express CD11a. These antibodies possess an CD11a-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO96/27011 published Sep. 6, 1996.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175:217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444–6448 (1993) has provided an alternative mechanism for making bispecific antibody fragments. The fragments comprise a heavy-chain variable domain ($V_H$) connected to a lightchain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.* 152:5368 (1994). Alternatively, the bispecific antibody may be a "linear antibody" produced as described in Zapata et al. *Protein Eng.* 8(10):1057–1062 (1995).

Antibodies with more than two valencies are contemplated. For example, trispecific antibodies can be prepared. Tutt et al., *J. Immunol.* 147:60 (1991).

(viii) Other Modifications

Other modifications of the humanized anti-CD11a antibody are contemplated. For example, it may be desirable to modify the antibody of the invention with respect to effector function, so as to enhance the effectiveness of the antibody in treating cancer, for example. For example cysteine residue (s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191–1195 (1992) and Shopes, B. *J. Immunol.* 148:2918–2922 (1992). Homodimeric antibodies with enhanced anti-tumor activity may also be prepared using heterobifunctional cross-linkers as described in Wolff et al., *Cancer Research* 53:2560–2565 (1993). Alternatively, an antibody can be engineered which has dual Fc regions and may thereby have enhanced complement lysis and ADCC capabilities. See Stevenson et al., *Anti-Cancer Drug Design* 3:219–230 (1989).

The invention also pertains to immunoconjugates comprising the antibody described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-CD11a antibodies. Examples include $^{212}$Bi, $^{131}$I, $^{131}$In, $^{90}$Y and $^{186}$Re.

Conjugates of the antibody and cytotoxic agent are made using a variety of bifunctional protein coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radio nuclide).

The anti-CD11a antibodies disclosed herein may also be formulated as immunoliposomes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem. 257:286–288 (1982) via a disulfide interchange reaction. A chemotherapeutic agent (such as Doxorubicin) is optionally contained within the liposome. See Gabizon et al., J. National Cancer Inst. 81(19):1484 (1989)

The antibody of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328:457–458 (1987)). Antibody-abzyme conjugates can be prepared as described herein for delivery of the abzyme to a tumor cell population.

The enzymes of this invention can be covalently bound to the anti-CD11a antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature 312:604–608 (1984)).

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO96/32478 published Oct. 17, 1996.

The salvage receptor binding epitope generally constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

In one most preferred embodiment, the salvage receptor binding epitope comprises the sequence (5' to 3'): PKNSSMISNTP (SEQ ID NO:16), and optionally further comprises a sequence selected from the group consisting of HQSLGTQ (SEQ ID NO:17), HQNLSDGK (SEQ ID NO:18), HQNISDGK (SEQ ID NO:19), or VISSHLGQ (SEQ ID NO:20), particularly where the antibody fragment is a Fab or F(ab')$_2$. In another most preferred embodiment, the salvage receptor binding epitope is a polypeptide containing the sequence(s) (5' to 3'): HQNLSDGK (SEQ ID NO:18), HQNISDGK (SEQ ID NO:19), or VISSHLGQ (SEQ ID NO:20) and the sequence: PKNSSMISNTP (SEQ ID NO:16).

Covalent modifications of the humanized CD11a antibody are also included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R-N=C=N-R'), where R and R' are different alkyl groups, such as 1-cyclohexyl-3-(2-morpholinyl4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79–86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, *CRC Crt. Rev. Biochem.*, pp. 259–306 (1981).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. *Arch. Biochem. Biophys.* 259:52 (1987) and by Edge et al. *Anal. Biochem.*, 118:131 (1981). Enzymatic cleavage of carbohydrate moieties on antibodies can be achieved by the use of a variety of endo- and exo-glycosidases as described by Thotakura et al. *Meth. Enzymol.* 138:350 (1987).

Another type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

B. Vectors, Host Cells and Recombinant Methods

The invention also provides isolated nucleic acid encoding the humanized anti-CD11a antibody, vectors and host cells comprising the nucleic acid, and recombinant techniques for the production of the antibody.

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The anti-CD11a antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-CD11a antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including Saccharomyces and Kluyveromyces α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the anti-CD11a antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-CD11a antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding anti-CD11a antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of Kluyveromyces yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968–975 (1991).

(iv) Promoter Component

Expression and cloning vectors usually contain a promoter that is recognized by the host organism and is operably linked to the anti-CD11a antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-CD11a antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-CD11a antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598–601 (1982) on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the anti-CD11a antibody of this invention by higher eukaryotes is often increased by inserting an enhancer sequence into the vector. Many enhancer sequences are now known from mammalian genes (globin, elastase, albumin, α-fetoprotein, and insulin).

Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the anti-CD11a antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-CD11a antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-CD11a antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; Kluyveromyces hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; yarrowia (EP 402,226); *Pichia pastoris* (EP 183,070); Candida; *Trichoderma reesia* (EP 244,234); *Neurospora crassa*; Schwanniomyces such as *Schwanniomyces occidentalis*; and filamentous fungi such as, e.g., Neurospora, Penicillium, Tolypocladium, and Aspergillus hosts such as *A. nidulans* and *A. niger*.

Suitable host cells for the expression of glycosylated anti-CD11a antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44–68 (1982)); MRC 5 cells; FS4 cells; and a human hepatoma line (Hep G2).

Host cells are transformed with the above-described expression or cloning vectors for anti-CD11a antibody production and cultured in conventional nutrient media modified as appropriate for inducing promoters, selecting transformants, or amplifying the genes encoding the desired sequences.

(viii) Culturing the Host Cells

The host cells used to produce the anti-CD11a antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Anti-CD11a Antibody

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology*

10:163–167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatents from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1–13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5–4.5, preferably performed at low salt concentrations (e.g.,from about 0–0.25M salt).

C. Pharmaceutical Formulations

Therapeutic formulations of the antibody are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsion;, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

D. Non-therapeutic Uses for the Antibody

The antibodies of the invention may be used as affinity purification agents. In this process, the antibodies are immobilized on a solid phase such a Sephadex resin or filter paper, using methods well known in the art. The immobilized antibody is contacted with a sample containing the CD11a protein (or fragment thereof) to be purified, and thereafter the support is washed with a suitable solvent that will remove substantially all the material in the sample except the CD11a protein, which is bound to the immobilized antibody. Finally, the support is washed with another suitable solvent, such as glycine buffer, pH 5.0, that will release the CD11a protein from the antibody.

Anti-CD11a antibodies may also be useful in diagnostic assays for CD11a protein, e.g., detecting its expression in specific cells, tissues, or serum.

For diagnostic applications, the antibody typically will be labeled with a detectable moiety. Numerous labels are available which can be generally grouped into the following categories:

(a) Radioisotopes, such as $^{35}$S, $^{14}$C, $^{125}$I, $^{3}$H, and $^{131}$I. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langone & H. Van Vunakis), Academic press, New York, 73:147–166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-CD11a antibody need not be labeled, and the presence thereof can be detected using a labeled antibody which binds to the CD11a antibody.

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc. 1987).

Competitive binding assays rely on the ability of a labeled standard to compete with the test sample analyte for binding with a limited amount of antibody. The amount of CD11a protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody is labeled with a radio nuclide (such as $^{111}$In, $^{99}$Tc, $^{14}$C, $^{131}$I, $^{125}$I, $^{3}$H, $^{32}$P or $^{35}$S) so that the tumor can be localized using immunoscintiography.

E. Diagnostic Kits

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. Therapeutic Uses for the Antibody

It is contemplated that the anti-CD11a antibody of the present invention may be used to treat the various LFA-1 mediated disorders as described herein.

The anti-CD11a antibody is administered by any suitable means, including parenteral, subcutaneous, intraperitoneal, intrapulmonary, and intranasal, and, if desired for local immunosuppressive treatment, intralesional administration (including perfusing or otherwise contacting the graft with the antibody before transplantation). Parenteral infusions include intramuscular, intravenous, intraarterial, intraperitoneal, or subcutaneous administration. In addition, the anti-CD11a antibody is suitably administered by pulse infusion, particularly with declining doses of the antibody. Preferably the dosing is given by injections, most preferably intravenous or subcutaneous injections, depending in part on whether the administration is brief or chronic.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 15 mg/kg (e.g., 0.1–20 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the LFA-1-mediated disorder, including treating rheumatoid arthritis, reducing inflammatory responses, inducing tolerance of immunostimulants, preventing an immune response that would result in rejection of a graft by a host or vice-versa, or prolonging survival of a transplanted graft. Such amount is preferably below the amount that is toxic to the host or renders the host significantly more susceptible to infections.

The antibody need not be, but is optionally formulated with one or more agents currently used to prevent or treat the disorder in question. For example, in rheumatoid arthritis, the antibody may be given in conjunction with a glucocorticosteroid. In addition, T cell receptor peptide therapy is suitably an adjunct therapy to prevent clinical signs of autoimmune encephalomyelitis. For transplants, the antibody may be administered concurrently with or separate from an immunosuppressive agent as defined above, e.g., cyclosporin A, to modulate the immunosuppressant effect. Alternatively, or in addition, VLA4 antagonists or other LFA-1 antagonists may be administered to the mammal suffering from a LFA-1 mediated disorder. The effective amount of such other agents depends on the amount of anti-CD11a antibody present in the formulation, the type of disorder or treatment, and other factors discussed above. These are generally used in the same dosages and with administration routes as used hereinbefore or about from 1 to 99% of the heretofore employed dosages.

G. Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-CD11a antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXAMPLE

PRODUCTION OF HUMANIZED ANTI-CD11a ANTIBODIES

This example describes the humanization and in vitro biological efficacy of a murine anti-human CD11a monoclonal antibody, MHM24 (Hildreth et al., *Eur. J. Immunol.* 13:202–208 (1983)). Previous studies on the murine MHM24 have shown that it, like other anti-CD11a antibodies, can inhibit T cell function (Hildreth et al., *J. Immunol.* 134:3272–3280 (1985); Dougherty et al., *Eur. J. Immunol.* 17:943–947 (1987)). Both the murine and humanized MAbs effectively prevent adhesion of human T cells to human keratinocytes and the proliferation of T cells in response to nonautologous leukocytes in the mixed lymphocytes response (MLR), a model for responsiveness to MHC class II antigens (McCabe et al., *Cellular Immunol.* 150:364–375 (1993)). However, both the murine (Reimann et al., *Cytometry*, 17:102–108 (1994)) and humanized MAbs did not cross-react with nonhuman primate CD11a other than chimpanzee CD11a. In order to have a humanized MAb available for preclinical studies in rhesus, the humanized MAb was re-engineered to bind to rhesus CD11a by changing four residues in one of the complementarity-determining regions, CDR-H2, in the variable heavy domain. Cloning and molecular modeling of the rhesus CD11a I-domain suggested that a change from a lysine residue in human CD11a I-domain to glutamic acid in rhesus CD11a I-domain is the reason that the murine and humanized MAbs do not bind rhesus CD11a.

Materials and Methods
(a) Construction of Humanized F(ab')s

The murine anti-human CD11a MAb, MHM24 (Hildreth et al., *Eur. J. Immunol.* 13:202–208 (1983); Hildreth et al., *J. Immunol.* 134:3272–3280 (1985)), was cloned and sequenced. In order to have a plasmid useful for mutagenesis as well as for expression of F(ab)s in *E. coli*, the phagemid pEMX1 was constructed. Based on the phagemid pb0720, a derivative of pB0475 (Cunningham et al., *Science* 243:13301336 (1989)), pEMX1 contains a DNA fragment encoding a humanized κ-subgroup I light chain and a humanized subgroup III heavy chain (VH-CH1) and an alkaline phosphatase promotor and Shine-Dalgamo sequence both derived from another previously described pUC119-based plasmid, pAK2 (Carter et al., *Proc. Natl. Acad. Sci. USA* 89:4285 (1992)). A unique SpeI restriction site was also introduced between the DNA encoding for the F(ab) light and heavy chains.

To construct the first F(ab) variant of humanized MHM24, F(ab)-1, site-directed mutagenesis (Kunkel, *Proc. Natl. Acad. Sci. USA* 82:488 (1985)) was performed on a deoxyuridine-containing template of pEMX1; all six CDRs were changed to the MHM24 sequence. All other F(ab) variants were constructed from a template of F(ab)-1. Plasmids were transformed into *E. coli* strain XL-1 Blue (Stratagene, San Diego, Calif.) for preparation of double- and single-stranded DNA. For each variant both light and heavy chains were completely sequenced using the dideoxynucleotide method (Sequenase, U.S. Biochemical Corp.). Plasmids were transformed into *E. coli* strain 16C9, a derivative of MM294, plated onto LB plates containing 5 µg/ml carbenicillin, and a single colony selected for protein expression. The single colony was grown in 5 ml LB-100 µg/ml carbenicillin for 58 h at 37° C. The 5 ml culture was added to 500 ml AP5100 µg/ml carbenicillin and allowed to grow for 16 h in a 4 L baffled shake flask at 37° C. APS media consists of: 1.5 g glucose, 11.0 Hycase SF, 0.6 g yeast extract (certified), 0.19 g MgSO4 (anhydrous), 1.07 g NH4Cl, 3.73 g KCl, 1.2 g NaCl, 120 ml 1 M triethanolamine, pH 7.4, to 1 L water and then sterile filtered through 0.1 µm Sealkeen filter.

Cells were harvested by centrifugation in a 1 L centrifuge bottle (Nalgene) at 3000×g and the supernatant removed. After freezing for 1 h, the pellet was resuspended in 25 ml cold 10 mM MES-10 mM EDTA, pH 5.0 (buffer A). 250 µl of 0.1 M PMSF (Sigma) was added to inhibit proteolysis and 3.5 ml of stock 10 mg/ml hen egg white lysozyme (Sigma) was added to aid lysis of the bacterial cell wall. After gentle shaking on ice for 1 h, the sample was centrifuged at 40,000×g for 15 min. The supernatant was brought to 50 ml with buffer A and loaded onto a 2 ml DEAE column equilibrated with buffer A. The flow-through was then applied to a protein G-Sepharose CL-4B (Pharmacia) column (0.5 ml bed volume) equilibrated with buffer A. The column was washed with 10 ml buffer A and eluted with 3 ml 0.3 M glycine, pH 3.0, into 1.25 ml 1 M Tris, pH 8.0. The F(ab) was then buffer exchanged into PBS using a Centricon-30 (Amicon) and concentrated to a final volume of 0.5 ml. SDS-PAGE gels of all F(ab)s were run to ascertain purity and the molecular weight of each variant was verified by electrospray mass spectrometry.

(b) Construction of Chimeric and Humanized IgG

For generation of human IgG1 variants of chimeric (chIgG1) and humanized (HuIgG1) MHM24, the appropriate murine or humanized variable light and variable heavy (F(ab)-8, Table II) domains were subcloned into separate previously described pRK vectors (Gorman et al., *DNA Protein Eng. Tech.* 2:3 (1990)). Alanine-scan variants were constructed by site-directed mutagenesis (Kunkel, *Proc. Natl. Acad. Sci. USA* 82:488 (1985)) of the HuIgG1 light and heavy chain plasmids. The DNA sequence of each variant was verified by dideoxynucleotide sequencing.

Heavy and light chain plasmids were cotransfected into an adenovirus-transformed human embryonic kidney cell line, 293 (Graham et al., *J. Gen. Virol.* 36:59 (1977)), using a high efficiency procedure (Graham et al., *J. Gen. Virol.* 36:59 (1977); Gorman et al., *Science*, 221:551 (1983)). Media was changed to serum-free and harvested daily for up to 5 days. Antibodies were purified from the pooled supernatents using protein A-Sepharose CL-4B (Pharmacia). The eluted antibody was buffer exchanged into PBS using a Centricon-30 (Amicon), concentrated to 0.5 ml, sterile filtered using a Millex-GV (Millipore) and stored at 4° C.

The concentration of antibody was determined using total Ig-binding ELISA. The concentration of the reference humanized anti-p185$^{HER}$IgG1 (Carter et al., *Proc. Natl. Acad. Sci. USA* 89:4285 (1992)) was determined by amino acid composition analysis. Each well of a 96-well plate was coated with 1 µg/ml of goat anti-human IgG F(ab')$_2$ (Cappel Laboratories, Westchester, Pa.) for 24 h at 4° C. Purified antibodies were diluted and added in duplicate to the coated plates. After 1.5 h incubation, the plates were washed with PBS-0.02% Tween 20 and 0.1 ml of a 1:2000 dilution of horseradish peroxidase-conjugated sheep anti-human IgG F(ab')$_2$ (Cappel) was added. After 1.5 h incubation the plates were washed and 0.1 ml 0.2 mg/ml o-phenylenediamine dihydrochloride-0.01% hydrogen peroxide-PBS was added. After 10 min. the reaction was stopped with 2 M sulfuric acid and the O.D. 490 nm was read.

(c) Cloning of Rhesus CD11a I-domain

The DNA sequence of the rhesus I-domain was obtained using RT-PCR and primers derived from the human CD11a DNA sequence. Briefly, mRNA was isolated from ~$10^7$ rhesus jK) leukocytes using the Fast Track mRNA purification kit (Invitrogen). 10 µg mRNA was reverse transcribed using MuLV reverse transcriptase. The first strand cDNA was then amplified by 40 cycles of PCR using the primers:

5'-CACTTTGGATACCGCGTCCTGCAGGT-3' (forward) (SEQ ID NO:21) and

5'-CATCCTGCAGGTCTGCCTTCAGGTCA-3' (reverse) (SEQ ID NO:22).

A single band of the predicted size was purified from the PCR reaction using agarose gel electrophoresis. The PCR product was digested with restriction enzyme Sse8387I (Takara) and ligated to a human CD11a-containing plasmid digested with the same restriction enzyme. There are two Sse8387I sites in the human CD11a sequence, one on either side of the I-domain. The resulting plasmid encoded a chimera consisting of human CD11a with a rhesus I-domain substituted for the human I-domain. DNA sequence analysis revealed five amino acid differences between human and rhesus. One difference was in the region N-terminal to the I-domain (Thr59Ser) and the other four differences were in the I-domain itself: Val133Ile, Arg189Gln, Lys197Glu, and Val308Ala (FIG. 2).

(d) FACScan Analysis of F(ab) and IgG Binding to Jurkat Cells

Aliquots of $10^6$ Jurkat T-cells were incubated with serial dilutions of humanized and control antibodies in PBS-0.1% BSA-10 mM sodium azide for 45 min at 4° C. The cells were washed and then incubated in fluorescein-conjugated goat anti-human F(ab')$_2$ (Organon Teknika, Westchester, Pa.) for 45 min at 4° C. Cells were washed and analysed on a FACScan (Becton Dickinson, Mountain View, Calif.). 8×$10^3$ cells were acquired by list mode and gated by forward light scatter versus side light scatter, thereby excluding dead cells and debris.

(e) Saturation Binding to Determine Apparent $K_0$s

Radiolabeled antibodies were prepared using Iodo-Gen (Pierce, Rockford, Ill.) according to the manufacturer's instructions. 50 μg of antibody and 1 mCi$^{125}$I (DuPont, Wilmington, Del.) were added to each tube and incubated for 15 min at 25° C. Radiolabeled proteins were purified from the remaining free $^{125}$I using PD-10 columns (Pharmacia, Uppsala, Sweden) equilibrated in Hank's Balanced Salt Solution (HBSS, Life Technologies, Grand Island, N.Y.) containing 0.2% gelatin.

Mononuclear cells were purified from heparinized human peripheral blood collected from two donors using Lymphocyte Separation Medium (LSM, Organon Teknika, Durham, N.C.) according to the manufacturer's instructions. The blood was centrifuged at 400×g for 40 min at 25° C. with no braking. Cells at the interface of the LSM and plasma were harvested and then resuspended in HBSS-0.2% gelatin.

Leukocytes were purified from heparinized rhesus monkey peripheral blood collected from two individuals by Dextran sedimentation. Blood was diluted with an equal volume of 3% Dextran T500 (Pharmacia) in PBS and was allowed to sediment undisturbed at 25° C. for 30 min. After sedimentation, cells remaining in suspension were harvested and pelleted by centrifugation at 400×g for 5 min. Residual erythrocytes were removed by two cycles of hypotonic lysis using distilled water and 2×HBSS. After erythrocyte lysis, cells were washed in PBS and then resuspended in HBSS-0.2% gelatin.

Antibody affinities were determined by saturation binding using either peripheral blood mononuclear cells (murine MHM24 and HuIgG1) or rhesus leukocytes (MHM23, RhIgG1). In each assay, a radiolabeled antibody was serially diluted in HBSS-0.2% gelatin in quadruplicate. Nonspecific binding was determined by the addition of 500 nM final concentration of homologous unlabeled antibody in duplicate through the serial dilution. Human lymphocytes or rhesus leukocytes were added to the plates in a volume of 170 μl per well. Plates were incubated for 2 hr at room temperature on an orbital plate shaker. After incubation, cells were harvested using a SKATRON™ cell harvester (Lier, Norway) and washed 10 times with PBS containing 0.25% gelatin and 0.1% sodium azide. Samples were then counted for 1 min in an LBK Wallac GammaMaster gamma counter (Gaithersburg, Md.). Data was transformed from counts per minute to nanomolarity and four-parameter curve-fitting of saturation plots (bound versus total) was then performed to determine $K_d$ (app) values.

(f) Keratinocyte Monolayer Adhesion Assay

Normal human epidermal keratinocytes (Clonetics, San Diego, Calif.) were removed from culture flasks with trypsin-EDTA, centrifuged, and resuspended in lymphocyte assay medium (RPMI 1640 (GIBCO)-10% fetal calf serum-1% penicillin/streptomycin) at a concentration of 5×10$^5$ viable cells/ml. Aliquots of 0.1 ml/well were then cultured overnight in flat-bottom 96-well plates; appropriate wells were stimulated by addition of interferon-gamma (Genentech, South San Francisco, Calif.) at 100 units/well.

Jurkat clone E6-1 cells (ATCC, Rockville, Md.) or purified rhesus lymphocytes (see MLR methods) were labeled with 20 μg/ml Calcein AM (Molecular Probes, Eugene, Oreg.) at 37° C. for 45 min. After washing three times with lymphocyte assay medium, Jurkat or rhesus lymphocyte cells were resuspended to 1×10$^6$ cells/ml and incubated with serially-diluted antibody at 4° C. for 30 min. After removal of medium from the keratinocyte monolayer, 0.1 ml/well of labeled cells were added and incubated at 37° C. for 1 h. The wells were washed five times with 0.2 ml/well/wash of 37° C. lymphocyte medium to remove non-attached cells. Fluorescence was measured using a Cytofluor 2300 (Millipore, Bedford, Mass.).

A rhesus-human chimeric CD11a (Rh/HuCD11a) comprising human CD11a with a rhesus I-domain was constructed by site-directed mutagenesis (Kunkel, *Proc. Natl. Acad. Sci. USA* 82:488 (1985)) on a deoxyuridine-containing template plasmid encoding human CD11a. Four residues were altered: Val133Ile, Arg189Gln, Lys197Glu, and Val308Ala (FIG. 2). Plasmids coding for Rh/HuCD11a and human CD11b (EP 364,690) were cotransfected into an adenovirus-transformed human embryonic kidney cell line, 293 (Graham et al., *J. Gen. Virol.* 36:59 (1977)), using a high efficiency procedure (Graham et al., *J. Gen. Viro.* 36:59 (1977); Gorman et al., *Science*, 221:551 (1983)). Rh/HuCD11a-transfected 293 cells were labeled with 20 μg/ml Calcein AM at 37° C. for 45 min. After washing three times with lymphocyte assay medium, Rh/HuCD11a-transfected 293 cells were resuspended to 1×10$^6$ cells/ml and incubated with serially-diluted antibody at 4° C. for 30 min. After removal of medium from the keratinocyte monolayer, 0.1 ml/well of labeled 293 cells was added and incubated at 37° C. for 1 h. The wells were washed five times with 0.2 ml/well/wash of 37° C. lymphocyte medium to remove non-attached cells. Fluorescence was measured using a Cytofluor 2300.

(g) ICAM Adhesion Assay

Maxisorp (Nunc) 96-well plates were coated with 0.1 ml/well of 1 μg/ml goat anti-human IgG Fc (Caltag) for 1 h at 37° C. After washing the plates three times with PBS, the plates were blocked with 1% BSA-PBS for 1 h at 25° C. The plates were then washed three times with PBS and 0.1 ml/well of 50 ng/ml recombinant human ICAM-IgG was added and incubated overnight.

The ICAM-IgG consisted of the five extracellular domains of human ICAM fused onto a human IgG Fc. A plasmid for the expression of a human ICAM-1 (Simmons et al. *Nature* 331:624627 (1988) and Staunton et al. *Cell* 52:925–933 (1988)) immunoadhesin called pRK.5dICAMGaIg was constructed. It contains the five Ig-like domains of ICAM-1, a six amino acid cleavage site recognized by an H64A variant of subtilisin BPN', Genenase I (Carter et al. *Proteins: Structure, Function and Genetics* 6:240–248 (1989)), and the Fc region from human IgG1 (Ellison et al. *Nucleic Acids Research* 10:4071–4079 (1982)) in the pRK5 vector (Eaton et al. *Biochemistry* 25:8343–8347 (1986)). Human embryonic kidney 293 cells (Graham et al. *J. Gen. Virol.* 36:59 (1977)) were stably transfected with pRK.5dICAMGaIg and the RSV-neo plasmid (Gorman et al. *Science* 221:551–553 (1983)) to generate a cell line expressing the five domain ICAM Ig (5dICAMIg). A clone was selected which expressed 20 μg/ml of secreted 5dICAMIg by enzyme-linked immunosorbent assay (ELISA), using antibodies to human IgG Fc (Caltag, Burlingame, Calif.) and ICAM-1 (BBIG-I1; R & D Systems, Minneapolis, Minn.). Cell culture supernatant from this cell line was loaded onto a Protein A column (ProsepA, Bioprocessing, Ltd., Durham, England) equilibrated in 0.01 M Hepes buffer (pH 7.0), 0.15 M NaCl (HBS) and the column was washed with HBS followed by 0.01 M Hepes buffer (pH 7.0), 0.5 M NaCl, 0.5 M TMAC (tetra-methyl ammonium chloride) to remove non-specifically bound material. The TMAC buffer was thoroughly washed from the column with HBS and the 5dICAMIg eluted with 0.01 M Hepes buffer (pH 7.0), 3.5 M MgCl2 and 10% (w/v) glycerol. The protein A pool was dialyzed extensively against HBS and concentrated.

Purified rhesus lymphocytes (see MLR methods) were labeled with 20 μg/ml Calcein AM (Molecular Probes, Eugene, Oreg.) at 37° C. for 45 min. After washing three times with lymphocyte assay medium, rhesus lymphocyte cells were resuspended to 1×10⁶ cells/ml and incubated with serially-diluted antibody at 4° C. for 30 min. After removal of medium from the ICAM-IgG coated plates, 0.1 ml/well of labeled cells were added and incubated at 37° C. for 1 h. The wells were washed five times with 0.2 ml/well/wash of 37° C. lymphocyte medium to remove non-attached cells. Fluorescence was measured using a Cytofluor 2300 (Millipore, Bedford, Mass.).

(h) One-way Mixed Lymphocyte Response (MLR)

For both human and rhesus MLR, peripheral blood lymphocytes from two unrelated donors were isolated from whole, heparinized blood using Lymphocyte Separation Medium (Organon Teknika, Durham, N.C.). Lymphocytes were resuspended to a concentration of 3×10⁶ cells/ml in RPMI 1640 (GIBCO)-10% human AB serum-1% glutamine-1% penicillin/streptomycin-1% non-essential amino acids-1% pyruvate-5×10⁻⁵ M 2-β-mercaptoethanol-50 μg/ml gentamycin-5 μg/ml polymyxin B. The stimulator cells were made unresponsive by irradiation with 3000 rads in a cesium irradiator. Responder cells at a concentration of 1.5×10⁵ cells per well were co-cultured with an equal number of stimulator cells in 96-well, flat-bottom plates. Serial two-fold dilutions of each antibody were added to the cultures to give a total volume of 200 μl/well. The cultures were incubated at 37° C. in 5% CO2 for 5 days and then pulsed with 1 μCi/well of [³H]thymidine for 16 h. [³H] thymidine incorporation was measured with a Beckman scintillation counter. Assays were done in triplicate. A humanized anti-human p185$^{HER2}$ MAb (Carter et al., Proc. Natl. Acad. Sci. USA 89:4285 (1992)) was used as isotype control for HuIgG1 and RhIgG1. A murine anti-hamster tPA MAb (Genentech) was used as isotype control (murine IgG1) for the MHM23 MAb. MAb 25.3 was purchased from Immunotech, Inc. (Westbrook, Me.).

(i) Computer Graphics Models of Murine and Humanized MHM24

Sequences of the VL and VH domains (FIGS. 1A & B) were used to construct a computer graphics model of the murine MHM24 VL-VH domains. This model was used to determine which framework residues should be incorporated into the humanized antibody. A model of F(ab)-8 was also constructed to verify correct selection of murine framework residues. Construction of the models was performed as described previously (Carter et al., Proc. Natl. Acad. Sci. USA 89:4285 (1992); Eigenbrot et al., J. Mol. Biol. 229:969 (1993)).

Results (a) Humanization

The consensus sequence for the human heavy chain subgroup III and the light chain subgroup kl were used as the framework for the humanization (Kabat et al., Sequences of Proteins of Immunological Interest. 5th Ed. Public Health Service, National Institutes of Health, Bethesda, Md. (1991)) (FIGS. 1A & B). This framework has been successfully used in the humanization of other murine antibodies (Carter et al., Proc. Natl. Acad. Sci. USA 89:4285 (1992); Presta et al., J. Immunol. 151:2623–2632 (1993); Eigenbrot et al., Proteins 18:49–62 (1994)). All humanized variants were initially made and screened for binding as F(ab)s expressed in E. coli. Typical yields from 500 ml shake flasks were 0.2–0.5 mg F(ab). Mass spectrometry verified the mass of each F(ab) to within 5 mass units.

CDR-H1 included residues H28–H35, which includes all exposed residues from both Kabat et al., Sequences of Proteins of Immunological Interest. 5th Ed. Public Health Service, National Institutes of Health, Bethesda, Md. (1991) and Chothia et al. Nature 342:877–883 (1989). The other hypervariable loops were defined according to Chothia et al. (1989). Light chain residue numbers are prefixed with L; heavy chain residue numbers are prefixed with H.

TABLE II

Binding of humanized MHM24 variants to human CD11a on Jurkat cells

| Variant | Template | Changes[a] | Purpose | EC50 F(ab)/EC50 F(ab)-2[b] Mean | S.D. | N |
|---|---|---|---|---|---|---|
| F(ab)-1 | Human FR | ArgH71Val | Straight CDR swap | no binding | | 2 |
| F(ab)-2 | F(ab)-1 | Ala H60Asn AspH61Gln SerH62Lys ValH63Phe GlyH65Asp | Extended CDR-H2 (Kabat et al. (1991)) | 1.0 | | 4 |
| F(ab)-3 | F(ab)-2 | PheH67Ala | Packing; CDR-H2 | 1.2 | 0.33 | 3 |
| F(ab)-4 | F(ab)-2 | ValH71Arg | Packing; CDR-H1,H2 | 2.9 | | 1 |
| F(ab)-5 | F(ab)-2 | AsnH73Lys LysH75Ser AsnH76Ser | Framework loop in VH | 0.043 | 0.015 | 4 |
| F(ab)-6 | F(ab)-5 | SerL53Thr GluL55Gln | Extended CDR-L2 | 0.012 | 0.005 | 4 |
| F(ab)-7 | F(ab)-6 | PheH27Tyr | Extended CDR-H1 | 0.004 | 0.002 | 4 |
| F(ab)-8 | F(ab)-7 | SerH75Lys SerH76Asn | Framework loop in VH | 0.004 | 0.002 | 4 |
| HuIgG1[c] | | | back to human | 0.004 | 0.002 | 4 |
| chIgG1[d] | | | | 0.006 | 0.005 | 4 |

[a]Murine residues are in bold; residue numbers are according to Kabat et al., Sequences of Proteins of Immunological Interest 5th Ed. Public Health Service, National Institutes of Health, Bethesda, MD (1991).
[b]Mean and standard deviation are the average of the ratios calculated for each of the independent FACScan assays; the EC50 for F(ab)-2 was 771 ± 320 ng/ml.
[c]HuIgG1 is F(ab)-8 VL and VH domains fused to human constant light and heavy chains.
[d]chIgG1 is chimeric IgG with murine VL and VH domains fused to human constant light and heavy chains.

In the initial variant F(ab)-1 the CDR residues were transferred from the murine antibody to the human framework. In addition, residue H71 was changed from the human Arg to murine Val since this residue has been shown previously to affect the conformations of CDR-H1 and CDR-H2 (Chothia et al., Nature, 342:877–883 (1989); Tramontano J. Mol. Biol. 215:175 (1990)). This F(ab) showed no detectable binding. In F(ab)-2 CDR-H2 was extended to include the sequence-based definition (i.e., including residues H60–H65). The EC50 for F(ab)-2 binding to human CD11a was 771±320 ng/ml, which was 148-fold weaker than the EC50 of the chimeric IgG1 (5.2±3.0 ng/ml).

In previous humanizations, it has been found that residues in a framework loop (FR-3) adjacent to CDR-H1 and CDR-H2 can affect binding (Eigenbrot et al., Proteins 18:49–62 (1994)). In F(ab)-5 three residues in this loop were changed to their murine counterpart and this variant showed a 23-fold improvement in binding (Table II). Alteration of human residues at positions L53 and L55 to murine (i.e. SerL53Thr and GluL55Gln) further improved binding by another 4-fold (F(ab)-6, Table II); this effectively converted CDR-L2 from the structure-based definition (residues L50–L52) to the sequence-based definition (residues L50–L56). Subsequent alteration of PheH27 to murine Tyr in CDR-H1 resulted in an additional 3-fold improvement (F(ab)-7; Table II). Finally, based on the models of murine and humanized MHM24, two of the three murine residues (H75 and H76) in FR-3 were changed back to human and it was found that these two residues had no effect on binding (cf. F(ab)-7 and F(ab)-8, Table II). The average EC50 for F(ab)-8 was slightly better than that of the chimeric IgG1 (Table II). Not all changes from human to murine resulted in improved binding. PheH67 was changed to murine Ala since this position had been previously found to affect binding (Presta et al., *J. Immunol.* 151:2623–2632 (1993)) but no effect was evident (F(ab)-3, Table II). Changing ValH71 back to the human Arg effected a 3-fold reduction in binding (F(ab)-4, Table II), supporting inclusion of ValH71 in F(ab)-1.

The VL and VH domains from F(ab)-8 were transferred to human IgG1 constant domains. The full length intact antibody, HuIgG1, showed an EC50 equivalent to F(ab)-8 and improved compared to the full length chimeric IgG1 (Table II). When data for all assays of HuIgG1 is considered, including its use as a standard for the alanine-scan and MLR assays (see below), the EC50 for HuIgG1 against human CD11a was 0.042±0.072 nM (N=15). Saturation binding analysis was also performed to determine the apparent dissociation constants, $K_d$(app): 0.15±0.02 nM for murine MHM24 and 0.15±0.04 nM for HuIgG1 (Table II).

TABLE III

Apparent $K_d$ by saturation binding to human lymphocytes and rhesus leukocytes

|  | muMHM24 $K_d$(app) nM | HuIgG1 $K_d$(app) nM | muMHM23 $K_d$(app) nM | RhIgG1 $K_d$(app) nM |
|---|---|---|---|---|
| human donor 1 | 0.16 +/- 0.01 | 0.11 +/- 0.08 |  |  |
| human donor 2 | 0.13 +/- 0.02 | 0.18 +/- 0.03 |  |  |
| rhesus donor 1 |  |  | 3.9 +/- 0.31 | 3.9 +/- 1.04 |
| rhesus donor 2 |  |  | 4.5 +/- 0.51 | n.d. |
| rhesus donor 3 |  |  |  | 2.8 +/- 1.1[a] |
| rhesus donor 3 |  |  |  | 2.7 +/- 0.9 |

[a] Assays of rhesus donor 3 were performed using two batches of RhIgG1; the assays were performed in the presence of 1 mg/ml human IgG1 to block Fc receptor interaction.

(b) Alanine-Scan of CDR Residues

To determine which CDR residues were involved in binding to human CD11a an alanine-scan (Cunningham et al., *Science* 244:1081 (1989)) was performed on the CDR residues of HuIgG1. Each variant was tested for binding to CD11a on Jurkat cells. In the light chain only CDR-L3 contributes to binding. HisL91 had a large effect (Table IV) and is probably conformational since this side chain should be partially buried. Residues AsnL92 and TyrL94 had more modest effect, reducing binding by 3-fold and 12-fold, respectively. Note however that simultaneously changing these two residues to alanine (as well as GluL93Ala) had a non-additive effect on binding (variant L3, Table IV).

TABLE IV

Alanine-scan of humanized MHM24 CDR residues

| Mutant IgG1 | CDR Sequence[a] | SEQ ID NO: | Human CD11a Var. EC50/HuIgG1 EC50[b] | | | Rhesus CD11a Var. EC50/HuIgG1 EC50[c] | | |
|---|---|---|---|---|---|---|---|---|
|  |  |  | Mean | S.D. | N | Mean | S.D. | N |
| CDR-H1 | GYSFTGHWMN | 25 |  |  |  |  |  |  |
| H1[d] | A A A | 26 | 5.9 | 0.8 | 2 | nb |  |  |
| SerH28Ala | A | 27 | 6.9 | 0.1 | 2 | nb |  |  |
| ThrH30Ala | A | 28 | 1.7 | 0.3 | 2 | 1.3 |  |  |
| GlyH31Ala | A | 29 | 1.2 | 0.1 | 2 | 2.4 |  |  |
| HisH32Ala | A | 30 | 2.3 | 0.2 | 2 | nb |  |  |
| TrpH33Ala | A | 31 | >870 |  | 1 | nb |  |  |
| CDR-H2 | MIHPSDSETRYNQKFKD | 32 |  |  |  |  |  |  |
| H2 | A A A | 33 | 14.1 | 7.8 | 10 | 0.055 | 0.050 | 15 |
| H2B | A A A | 34 | >600 |  | 2 | nb |  |  |
| H2A1 | A A | 35 | 10.8 | 7.3 | 6 | 0.013 | 0.012 | 10 |
| H2A2 | A A | 36 | 1.9 | 0.1 | 2 | 1.1 | 0.1 | 2 |
| H2A3 | A A | 37 | 4.6 | 0.2 | 2 | 1.3 |  |  |
| HisH52Ala | A | 38 | 1.5 | 0.2 | 2 | 0.7 |  |  |
| HisH52Ser | S | 39 | 5.0 | 0.3 | 2 | nb |  |  |
| SerH53Ala | A | 40 | 1.8 | 0.1 | 2 | 0.7 |  |  |
| AspH54Ala | A | 41 | 147 | 18 | 2 | 0.3 |  |  |
| SerH55Ala | A | 42 | 1.3 | 0.1 | 2 | 1.3 |  |  |
| SerH55Asn | N | 43 | 2.1 | 0.2 | 2 | nb |  |  |
| SerH55Gln | Q | 44 | 2.9 | 1.4 | 2 | 6.7 |  |  |
| GluH56Ala | A | 45 | 4.0 | 0.6 | 2 | 0.3 |  |  |
| ArgH58Ala | A | 46 | 1.1 | 0.1 | 2 | 3.3 |  |  |
| GlnH61Ala | A | 47 | 4.1 | 0.1 | 2 | 5.3 |  |  |
| LysH62Ala | A | 48 | 1.8 | 0.2 | 2 | 4.9 |  |  |
| LysH64Ala | A | 49 | 2.5 | 0.1 | 2 | 1.2 |  |  |
| AspH65Ala | A | 50 | 0.8 | 0.1 | 2 | 1.1 |  |  |
| FR-3 |  |  |  |  |  |  |  |  |
| LysH73Ala |  |  | 5.2 | 0.9 | 2 | nb |  |  |
| HysH73Arg |  |  | 4.6 | 1.1 | 2 | 5.5 |  |  |

TABLE IV-continued

Alanine-scan of humanized MHM24 CDR residues

| Mutant IgG1 | | SEQ ID NO: | Human CD11a Var. EC50/HuIgG1 EC50[b] | | | Rhesus CD11a Var. EC50/HuIgG1 EC50[c] | | |
|---|---|---|---|---|---|---|---|---|
| | CDR Sequence[a] | | Mean | S.D. | N | Mean | S.D. | N |
| CDR-H3 | GIYFYGTTYFD | 51 | | | | | | |
| H3 |   A  A | 52 | >900 | | 2 | nb | | |
| H3B |      AAA | 53 | 34.7 | 13.6 | 2 | nb | | |
| TyrH97Ala | A | 54 | 10.9 | 2.1 | 2 | nb | | |
| TyrH99Ala |   A | 55 | 1.4 | 0.1 | 2 | nb | | |
| ThrH100aAla |     A | 56 | 2.3 | 0.6 | 2 | nb | | |
| ThrH100bAla |      A | 57 | 1.4 | 0.2 | 2 | nb | | |
| TyrH100cAla |       A | 58 | 7.6 | 1.0 | 2 | nb | | |
| CDR-L1 | RASKTISKYLA | 59 | | | | | | |
| L1 | AA AA | 60 | 1.3 | 0.3 | 3 | 1.0 | | |
| CDR-L2 | SGSTLQS | 61 | | | | | | |
| L2 | A AA | 62 | 1.1 | 0.0 | 2 | nb | | |
| SerL50Ala | A | 63 | 1.2 | 0.5 | 2 | 2.7 | | |
| SerL52Ala |   A | 64 | 1.1 | 0.2 | 2 | 13.3 | | |
| ThrL53Ala |    A | 65 | 0.9 | 0.4 | 2 | 0.7 | | |
| CDR-L3 | QQHNEYPLT | 66 | | | | | | |
| L3 | AAA | 67 | >900 | | 2 | nb | | |
| HisL91Ala | A | 68 | >900 | | 2 | nb | | |
| AsnL92Ala |  A | 69 | 3.3 | 0.7 | 2 | 3.3 | | |
| GluL93Ala |   A | 70 | 1.7 | 0.2 | 2 | 2.9 | | |
| TyrL94Ala |    A | 71 | 11.8 | 0.1 | 2 | nb | | |
| hu4D5[e] | | | >900 | | 5 | nb | | |

[a]CDRs and FR-3 are as defined in Kabat et al., (1991) supra.
[b]EC50 HuIgG1 for human CD11a = 0.042 nM (S.D. = 0.072; N = 15).
[c]EC50 HuIgG1 for rhesus CD11a = 45.6 nM (S.D. = 40.4; N = 16); all values for rhesis CD11a are for a single binding assay unless otherwise noted; nb denotes binding of mutant is greater than 10-fold weaker than HuIgG1.
[d]Multiple alanine mutants:
H1, SerH28Ala/ThrH30Ala/HisH32Ala;
H2, HisH52Ala/SerH53Ala/SerH55Ala;
H2B, AspH54Ala/GluH56Ala/ArgH58Ala;
H2A1, HisH52Ala/SerH53Ala;
H2A2, SerH53Ala/SerH55Ala;
H2A3, HisH52Ala/SerH55Ala;
H3, TyrH97Ala/TyrH99Ala;
H3B, ThrH100aAla/ThrH100bAla/TyrH100cAla;
L1, LysL27Ala/ThrL28Ala/SerL30Ala/LysL31Ala;
L2, SerL50Ala/SerL52Ala/ThrL53Ala;
L3 AsnL92Ala/GluL93Ala/TyrL94Ala.
[e]hu4D5 is a humanized anti-p185[HER2] antibody with the same IgG1 framework as the huMNM24 antibody (Carter et al., Proc. Natl. Acad. Sci. USA 89:4285 (1992)).

In the heavy chain, CDR-H2 and CDR-H3 are the prominent contributors to the binding. CDR-H1 residue TrpH33Ala had a large effect but this is most likely due to a conformational change as TrpH33 should be partially buried. The most important single residue contributing to the binding is AspH54 in CDR-H2; changing this residue to alanine effected a 147-fold reduction in binding (Table IV). Other residues in CDR-H2 involved in binding include GluH56, GlnH61 and LysH64 (Table IV). In CDR-H3, TyrH97Ala reduced binding by 11-fold and TyrH100cAla by 8-fold. As in CDR-L3, simultaneous alteration of several CDR-H3 residues to alanine effected a non-additive, large reduction in binding (cf. variant H3 versus TyrH97Ala and TyrH99Ala, Table IV). In addition, the FR-3 residue included in the humanization, LysH73, also showed a 5-fold reduction in binding when changed to alanine or arginine (Table IV).

(c) Re-engineering HuIgG1 to Bind to Rhesus CD11a

Both murine MHM24 and HuIgG1 showed approximately 1000-fold reduction in binding to rhesus CD11a: HuIgG1 had an EC50 against rhesus CD11a of 45.6±40.4 nM (N=16) compared to an EC50 of 0.042±0.072 nM against human CD11a. Since a primate model is important in evaluating the biology, toxicity, and efficacy of MHM24, improving the binding of HuIgG1 to rhesus CD11a was deemed advantageous. Initially, the MAb hypervariable region residues which were important in binding to human CD11a and rhesus CD11a were determined so that those important for the rhesus but not the human could be altered. Accordingly, the alanine-scan variants were also assayed against rhesus CD11a on peripheral blood lymphocytes. The most important finding was that one of the multiple-alanine mutation variants, variant H2, bound 18-fold better to rhesus CD11a than HuIgG1 (Table IV). However, individual mutations at the three residues included in variant H2 showed minimal improvement in binding: HisH52Ala, 0.7-fold better, SerH53Ala, 0.7-fold better, and SerH55Ala, 1.3-fold worse (Table IV). A series of double mutations at these three residues showed that the combination HisH52Ala-SerH53Ala was the best, providing a 77-fold improvement in binding compared to HuIgG1 (cf. variants H2A1, H2A2 and H2A3, Table IV). In addition, the AspH54Ala and GluH56Ala variants also effected a 3-fold improvement over HuIgG1 (Table IV), even though AspH54 is the most important binding residue in HuIgG1 with respect to human CD11a.

In an attempt to find a single substitution at position H54 which would improve binding to rhesus CD11a but not reduce binding to human CD11a, position H54 was substituted with a variety of amino acids. All substitutions reduced binding by greater than an order of magnitude whereas the substitution AspH54Asn improved rhesus binding by 10-fold (Table V).

TABLE V

Amino acid substitution at AspH54

| AspH54 change to | Variant EC50/HuIgG1 EC50[a] | | |
|---|---|---|---|
| | Human CD11a[b] | | Rhesus CD11a[c] |
| | mean | S.D. | |
| Ala | 147 | 18 | 0.3 |
| Asn | 26 | 1 | 0.1 |
| Gln | 20 | 1 | 4.4 |
| Glu | 16 | 2 | >25 |
| Ser | >100 | | 0.9 |
| Arg | >250 | | >25 |
| Lys | >100 | | 3.8 |
| His | >300 | | >25 |
| Thr | >450 | | >25 |
| Met | >150 | | >25 |
| Leu | >300 | | >25 |

[a]EC50 HuIgG1 for human CD11a = 0.042 nM (S.D. = 0.072; N = 15); EC50 HuIgG1 for rhesus CD11a = 45.6 nM (S.D. = 40.4; N = 16).
[b]Values are the mean of two assays.
[c]Values are for a single assay.

Since non-additive effects were noted for changes at positions H52–H53, these were combined with a variety of changes at positions H54 and H56 (Table VI). For all variants, H52 and H53 were alanine. In one series, position H54 was Asn and position H56 was Glu (original), Ala, Asn or Gln. None of these variants improved rhesus CD11a binding over the H2A1 variant (Table VI). In another series, position H54 was Ala and position H56 was Glu (original), Ala, Ser or Asn and again all were worse than variant H2A1. In the third series, position H54 was Ser and position H56 was Glu (original), Ala, Ser or Asn. Two of these variants exhibited improved binding to rhesus CD11a compared to the H2A1 variant (H2C11 and H2C12 Table VI). The rhesus CD11a EC50 for these two variants was 0.11±0.11 nM (N=9) for H2C11 and 0.19±0.08 nM (N=7) for H2C12. These values are 3- to 5-fold weaker than the EC50 of HuIgG1 for human CD11a (0.042 nM) but are a 240- to 415-fold improvement over the EC50 of HuIgG1 for rhesus CD11a (45.6 nM). H2C12 will hereafter be referred to as RhIgG1. Apparent $K_d$ values from saturation binding experiments showed that RhIgG1 bound to rhesus CD11a as well as murine MHM23 bound to rhesus CD18 (Table III).

TABLE VI

Binding of CDR-H2 variants to human and rhesus CD11a

| Variant IgG1 | Sequence | Var.EC50/HuIgG1 EC50[a] | | |
|---|---|---|---|---|
| | | Human CD11a | Rhesus CD11a | |
| | | | Mean | S.D. |
| H2C2 | A | 2.6 | >100 | |
| H2C3 | AAAN | >100 | >100 | |
| CDR-H2 | MIHPSDSETRY | 1.0 | 1.00 | |
| H2A1 | A A | 10.8 | 0.013 | 0.012 (N = 10) |
| H2C1 | A AN | >100 | 0.56 | 0.01 |
| H2C4 | A AN A | >100 | 0.38 | 0.06 |
| H2C5 | A AN N | 46 | 0.11 | 0.02 |
| H2C6 | A AN Q | >100 | 0.21 | 0.01 |
| H2C8 | A AA | 12.7 | 0.38 | |
| H2C7 | A AA A | 2.4 | 1.03 | 0.05 |
| H2C10 | A AA S | 14.2 | 0.22 | 0.03 |
| H2C9 | A AA N | 34.3 | 0.22 | 0.04 |
| H2C13 | A AS | | 0.10 | 0.06 |
| H2C14 | A AS A | | 0.021 | 0.013 |
| H2C12 | A AS S | | 0.004 | 0.001 (N = 7) |
| H2C11 | A AS N | 24.9 | 0.002 | 0.001 (N = 9) |

[a]EC50 HuIgG1 for human CD11a = 0.042 nM (S.D. = 0.072; N = 15); EC50 HuIgG1 for rhesus CD11a = 45.6 nM (S.D. = 40.4; N = 16); all values for rhesus CD11a are the mean of two independent binding assays except as noted.

For the HuIgG1-human CD11a interaction, AspH54 was the most important residue (Table IV); changing this residue to other amino acids significantly reduced binding with the least reduction occurring for changes to Glu, Asn and Gln. However, for the HuIgG1-rhesus CD11a interaction, AspH54 was deleterious since changing this residue to Ala or Asn improved binding (Table V). In order to understand this difference between binding to human and rhesus CD11a, the latter was cloned from a rhesus PBL library. FIG. 2 shows that rhesus CD11a I-domain differs from human CD11a I-domain at only four positions: 133, 189, 197, 308. Previously the human CD11a epitope of MHM24 was mapped to residues 197–203 (Champe et al., *J. Biol. Chem.* 270:1388–1394 (1995)) which includes the human Lys197 to rhesus Glu197 change in rhesus.

(d) Keratinocyte Cell Adhesion Assays

Murine MHM24, chimeric IgG1 and HuIgG1 were compared in their ability to prevent adhesion of Jurkat cells (human T-cells expressing LFA-1) to normal human epidermal keratinocytes expressing ICAM-1. All three antibodies performed similarly (FIG. 3) with similar IC50 values (Table VII).

TABLE VII

Blocking of cell adhesion by MHM24 variants

| | | IC50 Value (nM) | | | | | | | |
|---|---|---|---|---|---|---|---|---|---|
| | | RhLy[b]:HuK | | | RhLy:HuICAM[c] | | | Rh/HuCD11a[d]:HuK | |
| mAb | Jurkat:HuK[a] | Mean | S.D. | N | Mean | S.D. | N | Mean | S.D. | N |
| murMHM24 | 0.09 | | | | | | | | | |
| HuIgG1 | 0.13 | | | | | | | | | |
| chIgG1 | 0.10 | | | | | | | | | |
| RhIgG1 | | 119 | 86 | 4 | 5.3 | 4.5 | 3 | 4.9 | 0.2 | 2 |
| MHM23 | | 1.6 | 1.5 | 3 | 1.2 | | | 1.4 | 0.1 | 2 |

[a]HuK = normal human epidermal keratinocyte.
[b]RhLy = rhesus lymphocyte.
[c]HuICAM = recombinant human ICAM-1.
[d]Rh/HuCD11a = human CD11a with rhesus I-domain transfected into human 293 cells.

Neither murine nor humanized MHM24 blocked rhesus or cynomolgus lymphocytes from adhering to human keratinocytes. When RhIgG1 was compared to the murine anti-human CD18 antibody MHM23 (Hildreth et al., *Eur. J. Immunol.* 13:202–208 (1983); Hildreth et al., *J. Immunol.* 134:3272–3280 (1985)) in blocking adherence of rhesus lymphocytes to human keratinocytes, RhIgG1 was 74-fold less efficacious than MHM23 (FIG. 4A, Table VII). However, when recombinant human ICAM-1 was coated on plates (instead of human keratinocytes) RhIgG1 was only 4-fold less efficacious than MHM23 (FIG. 4B, Table VII). A chimeric CD11a comprised of human CD11a in which the I-domain was mutated to rhesus (Val133Ile, Arg189Gln, Lys197Glu, Val308Ala) was transfected into human embryonic kidney 293 cells. Again, RhIgG1 was only 4-fold down from MHM23 in blocking these Rh/HuCD11a-293 cells from adhering to human keratinocytes (FIG. 4C, Table VII).

Control isotype antibodies for RhIgG1 (humanized anti-p185HER2 antibody; Carter et al., *Proc. Natl. Acad. Sci. USA* 89:4285 (1992)) and MHM23 (murine MAb 354, a murine IgG1 anti-hamster tPA) did not block binding of rhesus lymphocytes to human keratinocytes or recombinant ICAM-1 (FIGS. 4A, 4B) or Rh/HuCD11a to human keratinocytes (FIG. 4C). This implies that the reduced performance of RhIgG1 compared to murine MHM23 in the rhesus lymphocyte:human keratinocyte assay was not due to any unexpected interaction of the human Fc of HuIgG1 (compared to the murine Fc of MHM23) with the rhesus lymphocytes, which might reduce the concentration of RhIgG1 available for binding to rhesus CD11a. The recombinant human ICAM-1 data show that RhIgG1 is binding to the rhesus lymphocytes and preventing adherence almost as well as murine MHM23 (FIG. 4B, Table VII). The Rh/HuCD11a-293 data (FIG. 4C, Table VII) show that RhIgG1 is not binding to targets on the human keratinocytes (compared to HuIgG1), which might reduce the concentration of RhIgG1 available for binding to rhesus CD11a. In addition, the $K_d$(app) of RhIgG1 to rhesus leukocytes was similar with (rhesus donor 3) and without (rhesus donor 1) addition of 1 mg/ml human IgG1 (Table III); This shows that binding of RhIgG1 is specific to rhesus CD11a.

(e) Mixed Lymphocyte Response Assays

In the MLR, HuIgG1 exhibited an IC50 value 2-fold weaker than the murine MHM24 (Table VIII, FIG. 5).

TABLE VIII

Mixed lymphocyte response assay results

| | IC50 Value (nM) | | |
|---|---|---|---|
| mAb[a] | Mean | S.D. | N |
| murMHM24 | 0.19 | 0.06 | 3 |
| HuIgG1 | 0.38 | 0.14 | 4 |
| mAb 25.3 | 3.8 | 1.0 | 2 |
| RhIgG1 | 23.4 | 11.4 | 2 |
| MHM23 | 30.4 | 24.0 | 3 |

[a]murMHM24, HuIgG1 and mAb 25.3 tested in human MLR; RhIgG1 and MHM23 tested in rhesus MLR.

Both the murine and humanized MAbs fared 10- to 20-fold better than MAb 25.3, which has been previously tested in vivo (Fischer et al., *Blood* 77:249–256 (1991); Stoppa et al., *Transplant Intl.* 4:3–7 (1991); Hourmant et al., *Transplantation* 58:377–380 (1994)). The rhesus-binding variant RhIgG1 exhibited an IC50 value slightly better than murine MHM23 (Table VIII). Different responder:stimulator blood donors were used in independent assays and the results did not vary significantly. The $K_d$ of RhIgG1 for rhesus CD11a is about 26-fold down from the $K_d$ of HuIgG1 for human CD11a (Table III) and this is reflected in the IC50 values derived from the MLR assays (Table VIII).

What is claimed is:

1. A method of treating asthma in a patient in need thereof, comprising administering to the patient a therapeutically effective amount of a humanized anti-CD11a antibody which binds specifically to human CD11a I-domain, said antibody containing a heavy chain variable region comprising the amino acid sequence of (a) CDR1 (SEQ ID NO:10), CDR2 (SEQ ID NO:11) and CDR3 (SEQ ID NO:12) or (b) SEQ ID NO:5, and a light chain variable region comprising the amino acid sequence of (a) CDR1 (SEQ ID NO:13), CDR2 (SEQ ID NO:14) and CDR3 (SEQ ID NO:15) or (b) SEQ ID NO:2.

2. A method of treating graft versus host disease or host versus graft disease in an allogeneic transplantation in a patient in need thereof, comprising administering to the patient a therapeutically effective amount of a humanized anti-CD11a antibody which binds specifically to human CD11a I-domain, said antibody containing a heavy chain variable region comprising the amino acid sequence of (a) CDR1 (SEQ ID NO:10), CDR2 (SEQ ID NO:11) and CDR3 (SEQ ID NO:12) or (b) SEQ ID NO:5, and a ligit chain variable region comprising the amino acid sequence of (a) CDR1 (SEQ ID NO:13), CDR2 (SEQ ID NO:14) and CDR3 (SEQ ID NO:15) or (b) SEQ ID NO:2.

3. The method of claim 1 or claim 2 wherein the humanized anti-CD11a antibody has all human kappa I consensus light chain framework residues.

4. The method of claim 1 or claim 2 wherein the humanized anti-CD11a antibody has human $V_H$ subgroup III consensus heavy chain framework residue 93H.

5. The method of claim 1 or claim 2 wherein the humanized anti-CD11a antibody has a heavy chain variable region comprising the amino acid sequence of SEQ ID NO:5 and a light chain variable region comprising the amino acid sequence of SEQ ID NO:2.

6. The method of claim 1 or claim 2 wherein the humanized anti-CD11a antibody is a full length antibody.

7. The method of claim 6 wherein the humanized anti-CD11a antibody is a human IgG.

8. The method of claim 1 or claim 2 wherein the humanized anti-CD11a antibody is bound to a cytotoxic agent.

9. A method of treating psoriasis in a patient in need thereof, comprising administering to the patient a therapeutically effective amount of a humanized anti-CD11a antibody which binds specifically to human CD11a I-domain, said antibody containing a heavy chain variable region comprising the amino acid sequence of (a) CDR1 (SEQ ID NO:10), CDR2 (SEQ ID NO:11) and CDR3 (SEQ ID NO:12) or (b) SEQ ED NO:5, and a light chain variable region comprising the amino acid sequence of (a) CDR1 (SEQ ID NO:13), CDR2 (SEQ ID NO:14) and CDR3 (SEQ ID NO:15) or (b) SEQ ID NO:2.

10. The method of claim 9 wherein the humanized anti-CD11a antibody has a heavy chain variable region comprising the amino acid sequence of SEQ ID NO:5 and a light chain variable region comprising the amino acid sequence of SEQ ID NO:2.

11. The method of claim 9 wherein the humanized anti-CD11a antibody is a human IgG.

* * * * *

UNITED STATES PATENT AND TRADEMARK OFFICE
CERTIFICATE OF CORRECTION

PATENT NO. : 6,703,018 B2
DATED : March 9, 2004
INVENTOR(S) : Paula M. Jardieu and Leonard G. Presta It is certified that error appears in the above-identified patent and that said Letters Patent is hereby corrected as shown below:

Column 77,
Lines 13-24, Claim 2 should read as follows:

A method of treating graft versus host disease or host versus graft disease in an allogeneic transplantation in a patient in need thereof, comprising administering to the patient a therapeutically effective amount of a humanized anti-CD11a antibody which binds specifically to human CD11 a I-domain, said antibody containing a heavy chain variable region comprising the amino acid sequence of (a) CDR1 (SEQ ID NO:10), CDR2 (SEQ ID NO:11) and CDR3 (SEQ ID N0:12) or (b) SEQ ID N0:5, and a light chain variable region comprising the amino acid sequence of (a) CDR1 (SEQ ID NO:13) , CDR2 (SEQ ID NO:14) and CDR3 (SEQ ID NO:15) or (b) SEQ ID NO:2.

Column 78,
Lines 11-21, Claim 9 should read as follows:

A method of treating psoriasis in a patient in need thereof, comprising administering to the patient a therapeutically effective amount of a humanized anti-CD11a antibody which binds specifically to human CD11a I-domain, said antibody containing a heavy chain variable region comprising the amino acid sequence of (a) CDR1 (SEQ ID NO:10), CDR2 (SEQ ID NO:11) and CDR3 (SEQ ID NO:12) or (b) SEQ ID NO:5, and a light chain variable region comprising the amino acid sequence of (a) CDR1 (SEQ ID NO:13), CDR2 (SEQ ID NO: 14) and CDR3 (SEQ ID NO:15) or (b) SEQ ID NO:2.

Signed and Sealed this

Twenty-second Day of June, 2004

JON W. DUDAS
*Acting Director of the United States Patent and Trademark Office*